(12) United States Patent
Peterman et al.

(10) Patent No.: US 11,890,202 B2
(45) Date of Patent: Feb. 6, 2024

(54) SPINAL OSTEOTOMY

(71) Applicant: 3SPINE SEZC, Grand Cayman (KY)

(72) Inventors: Marc M Peterman, Duxbury, MA (US); Steven C Humphreys, Chattanooga, TN (US); Scott Hodges, Soldatna, AK (US)

(73) Assignee: 3SPINE, INC., Chattanooga, TN (US)

( * ) Notice: Subject to any disclaimer, the term of this patent is extended or adjusted under 35 U.S.C. 154(b) by 621 days.

(21) Appl. No.: 17/023,864

(22) Filed: Sep. 17, 2020

(65) Prior Publication Data

US 2021/0059832 A1 Mar. 4, 2021

Related U.S. Application Data

(60) Continuation of application No. 15/955,611, filed on Apr. 17, 2018, now Pat. No. 10,821,003, which is a continuation-in-part of application No. 15/712,046, filed on Sep. 21, 2017, now Pat. No. 10,631,995, which is a continuation of application No. 14/486,065, filed on Sep. 15, 2014, now Pat. No.
(Continued)

(51) Int. Cl.
*A61F 2/44* (2006.01)
*A61F 2/30* (2006.01)
*A61B 17/70* (2006.01)

(52) U.S. Cl.
CPC .......... *A61F 2/442* (2013.01); *A61F 2/4405* (2013.01); *A61F 2/4425* (2013.01); *A61B 17/7001* (2013.01); *A61F 2002/30331* (2013.01); *A61F 2002/30563* (2013.01); *A61F 2002/30578* (2013.01); *A61F 2002/30624* (2013.01); *A61F 2002/30652* (2013.01); *A61F 2002/30654* (2013.01); *A61F 2002/30662* (2013.01); *A61F 2002/30884* (2013.01); *A61F 2002/448* (2013.01); *A61F 2220/0033* (2013.01); *A61F 2250/0004* (2013.01); *A61F 2310/00796* (2013.01); *A61F 2310/00976* (2013.01)

(58) Field of Classification Search
CPC ....... A61F 2/4405; A61F 2/4425; A61F 2/443
See application file for complete search history.

(56) References Cited

U.S. PATENT DOCUMENTS 3,320,951 A 5/1967 Wittebol
3,510,883 A 5/1970 Cathcart, III
(Continued)

FOREIGN PATENT DOCUMENTS

CA 2552361 A1 8/2005
CH 624573 A5 8/1981
(Continued)

OTHER PUBLICATIONS

PCT—International Searching Authority, International Search Report and Written Opinion of the International Searching Authority for PCT/US2005/000648, dated Jun. 6, 2005, 12 pages.
(Continued)

*Primary Examiner* — Ellen C Hammond
(74) *Attorney, Agent, or Firm* — BRAINSPARK ASSOCIATES, LLC

(57) ABSTRACT

Disclosed are systems, devices, methods and surgical procedures for altering and/or correcting the alignment of adjacent bones, including bones of the spine.

17 Claims, 20 Drawing Sheets

Related U.S. Application Data 9,770,338, which is a division of application No. 11/839,821, filed on Aug. 16, 2007, now Pat. No. 8,864,832, which is a continuation of application No. 11/757,084, filed on Jun. 20, 2007, now abandoned.

(60) Provisional application No. 62/654,963, filed on Apr. 9, 2018, provisional application No. 62/486,329, filed on Apr. 17, 2017.

(56) References Cited

U.S. PATENT DOCUMENTS

| | | |
|---|---|---|
| 3,740,769 A | 6/1973 | Haboush |
| 3,903,549 A | 9/1975 | Deyerle |
| 4,309,777 A | 1/1982 | Patil |
| 4,349,921 A | 9/1982 | Kuntz |
| 4,470,158 A | 9/1984 | Pappas et al. |
| 4,550,450 A | 11/1985 | Kinnett |
| 4,622,959 A | 11/1986 | Marcus |
| 4,653,487 A | 3/1987 | Maale |
| 4,681,589 A | 7/1987 | Tronzo |
| 4,697,582 A | 10/1987 | William |
| 4,697,586 A | 10/1987 | Gazale |
| 4,702,930 A | 10/1987 | Heide et al. |
| 4,743,262 A | 5/1988 | Tronzo |
| 4,759,766 A | 7/1988 | Buettner-Janz |
| 4,759,769 A | 7/1988 | Hedman et al. |
| 4,805,607 A | 2/1989 | Englehardt et al. |
| 4,836,196 A | 6/1989 | Park et al. |
| 4,874,389 A | 10/1989 | Downey |
| 4,875,474 A | 10/1989 | Border |
| 4,892,545 A | 1/1990 | Day et al. |
| 4,946,378 A | 4/1990 | Hirayama |
| 4,932,975 A | 6/1990 | Main et al. |
| 4,997,432 A | 3/1991 | Keller |
| 5,004,476 A | 4/1991 | Cook |
| 5,037,438 A | 8/1991 | Davidson |
| 5,062,850 A | 11/1991 | MacMillan et al. |
| 5,071,437 A | 12/1991 | Steffee |
| 5,092,866 A | 3/1992 | Breard |
| 5,108,442 A | 4/1992 | Smith |
| 5,122,130 A | 6/1992 | Keller |
| 5,258,031 A | 11/1993 | Salib et al. |
| 5,271,737 A | 12/1993 | Baldwin et al. |
| 5,282,863 A | 2/1994 | Burton |
| 5,282,868 A | 2/1994 | Bahler |
| 5,290,312 A | 3/1994 | Kojimoto et al. |
| 5,314,477 A | 5/1994 | Marnay |
| 5,344,458 A | 9/1994 | Bonutti |
| 5,387,213 A | 2/1995 | Breard et al. |
| 5,401,269 A | 5/1995 | Buttner-Janz et al. |
| 5,415,661 A | 5/1995 | Holmes |
| 5,423,825 A | 6/1995 | Levine |
| 5,425,773 A | 6/1995 | Boyd et al. |
| 5,443,513 A | 8/1995 | Moumene et al. |
| 5,443,515 A | 8/1995 | Cohen et al. |
| 5,507,816 A | 4/1996 | Bullivant |
| 5,509,934 A | 4/1996 | Cohen |
| 5,534,029 A | 7/1996 | Shima |
| 5,534,030 A | 7/1996 | Navarro et al. |
| 5,554,191 A | 9/1996 | Lahille et al. |
| 5,554,194 A | 9/1996 | Sanders |
| 5,556,431 A | 9/1996 | Buttner-Janz |
| 5,562,660 A | 10/1996 | Grob |
| 5,562,737 A | 10/1996 | Graf |
| 5,562,738 A | 10/1996 | Boyd et al. |
| 5,571,109 A | 11/1996 | Bertangoli |
| 5,571,190 A | 11/1996 | Ulrich et al. |
| 5,591,235 A | 1/1997 | Kuslich |
| 5,607,425 A | 3/1997 | Rogozinski |
| 5,609,638 A | 3/1997 | Price et al. |
| 5,683,465 A | 4/1997 | Shinn et al. |
| 5,658,347 A | 8/1997 | Sarkisian et al. |
| 5,672,175 A | 9/1997 | Martin |
| 5,674,294 A | 10/1997 | Bainville |
| 5,674,296 A | 10/1997 | Bryan et al. |
| 5,676,701 A | 10/1997 | Yuan et al. |
| 5,702,450 A | 12/1997 | Bisserie |
| 5,702,469 A | 12/1997 | Whipple et al. |
| 5,728,098 A | 3/1998 | Sherman et al. |
| 5,752,957 A | 5/1998 | Ralph et al. |
| 5,755,811 A | 5/1998 | Tanamal et al. |
| 5,772,661 A | 6/1998 | Michelson |
| 5,800,547 A | 9/1998 | Shafer et al. |
| 5,824,093 A | 10/1998 | Ray et al. |
| 5,824,094 A | 10/1998 | Serhan et al. |
| 5,888,222 A | 3/1999 | Coates et al. |
| 5,895,428 A | 4/1999 | Berry |
| 5,899,941 A | 5/1999 | Nishijima et al. |
| RE36,221 E | 6/1999 | Breard et al. |
| 5,928,284 A | 7/1999 | Mehdizadeh |
| 5,961,516 A | 10/1999 | Graf |
| 6,010,502 A | 1/2000 | Bagby |
| 6,019,792 A | 2/2000 | Cauthen |
| 6,039,763 A | 3/2000 | Shelokov |
| 6,042,582 A | 3/2000 | Ray |
| RE36,758 E | 6/2000 | Fitz |
| 6,096,080 A | 8/2000 | Nicholson et al. |
| 6,102,954 A | 8/2000 | Albrektsson et al. |
| 6,106,557 A | 8/2000 | Robioneck et al. |
| 6,113,637 A | 9/2000 | Gill et al. |
| 6,113,638 A | 9/2000 | Williams et al. |
| 6,132,464 A | 10/2000 | Martin |
| 6,146,421 A | 11/2000 | Gordon et al. |
| 6,156,067 A | 12/2000 | Bryan et al. |
| 6,159,211 A | 12/2000 | Boriani et al. |
| 6,159,214 A | 12/2000 | Michelson |
| 6,159,244 A | 12/2000 | Suddaby |
| 6,174,311 B1 | 1/2001 | Branch et al. |
| 6,179,874 B1 | 1/2001 | Cauthen |
| 6,179,875 B1 | 1/2001 | Strempel |
| 6,190,414 B1 | 2/2001 | Young et al. |
| 6,193,757 B1 | 2/2001 | Foley et al. |
| 6,200,322 B1 | 3/2001 | Branch et al. |
| 6,224,599 B1 | 5/2001 | Baynham et al. |
| 6,224,607 B1 | 5/2001 | Michelson |
| 6,228,118 B1 | 5/2001 | Gordon |
| 6,231,609 B1 | 5/2001 | Mehdizadeh |
| 6,235,059 B1 | 5/2001 | Benezech et al. |
| 6,238,396 B1 | 5/2001 | Lombardo |
| 6,251,112 B1 | 6/2001 | Jackson |
| 6,251,140 B1 | 6/2001 | Marino et al. |
| 6,264,655 B1 | 7/2001 | Pisharodi |
| 6,277,122 B1 | 8/2001 | McGahan et al. |
| 6,325,827 B1 | 12/2001 | Lin |
| 6,368,350 B1 | 4/2002 | Erickson et al. |
| 6,368,353 B1 | 4/2002 | Arcand |
| 6,375,681 B1 | 4/2002 | Truscott |
| 6,387,130 B1 | 5/2002 | Stone et al. |
| 6,402,750 B1 | 6/2002 | Atkinson et al. |
| 6,402,785 B1 | 6/2002 | Zdeblick et al. |
| 6,409,766 B1 | 6/2002 | Brett |
| 6,413,278 B1 | 7/2002 | Marchosky |
| 6,419,703 B1 | 7/2002 | Fallin et al. |
| 6,419,705 B1 | 7/2002 | Erickson |
| 6,432,140 B1 | 8/2002 | Lin |
| 6,440,139 B2 | 8/2002 | Michelson |
| 6,440,168 B1 | 8/2002 | Cauthen |
| 6,454,807 B1 | 9/2002 | Jackson |
| 6,471,724 B2 | 10/2002 | Zdeblick et al. |
| 6,514,260 B1 | 2/2003 | Zdeblick et al. |
| 6,517,580 B1 | 2/2003 | Ramadan et al. |
| 6,524,312 B2 | 2/2003 | Landry et al. |
| 6,527,804 B1 | 3/2003 | Gauchet et al. |
| 6,540,747 B1 | 4/2003 | Marino |
| 6,540,785 B1 | 4/2003 | Gill et al. |
| 6,562,074 B2 | 5/2003 | Gerbec et al. |
| 6,565,571 B1 | 5/2003 | Jackowski et al. |
| 6,565,574 B2 | 5/2003 | Michelson |
| 6,565,605 B2 | 5/2003 | Goble et al. |
| 6,572,653 B1 | 6/2003 | Simonson |
| 6,579,319 B2 | 6/2003 | Goble et al. |
| 6,582,466 B1 | 6/2003 | Gauchet |
| 6,582,468 B1 | 6/2003 | Gauchet |

(56) References Cited

U.S. PATENT DOCUMENTS

| | | |
|---|---|---|
| 6,589,247 B2 | 7/2003 | McGahan et al. |
| 6,599,291 B1 | 7/2003 | Foley et al. |
| 6,607,557 B1 | 8/2003 | Brosnahan et al. |
| 6,610,065 B1 | 8/2003 | Branch et al. |
| 6,610,091 B1 | 8/2003 | Reiley |
| 6,610,093 B1 | 8/2003 | Pisharodi |
| 6,641,582 B1 | 11/2003 | Hanson et al. |
| 6,641,614 B1 | 11/2003 | Wagner et al. |
| 6,648,895 B2 | 11/2003 | Burkus et al. |
| 6,669,729 B2 | 12/2003 | Chin |
| 6,679,915 B1 | 1/2004 | Cauthen |
| 6,685,742 B1 | 2/2004 | Jackson |
| 6,692,495 B1 | 2/2004 | Zacouto |
| 6,699,247 B2 | 3/2004 | Zuckerman et al. |
| 6,709,458 B2 | 3/2004 | Michelson |
| 6,733,532 B1 | 5/2004 | Gauchet et al. |
| 6,740,118 B2 | 5/2004 | Eisermann et al. |
| 6,743,255 B2 | 6/2004 | Ferree |
| 6,749,635 B1 | 6/2004 | Bryan |
| 6,780,186 B2 | 8/2004 | Errrico et al. |
| 6,805,714 B2 | 10/2004 | Sutcliffe |
| 6,811,567 B2 | 11/2004 | Reily |
| 6,908,484 B2 | 6/2005 | Zubok et al. |
| 6,936,071 B1 | 8/2005 | Marnay et al. |
| 6,949,123 B2 | 9/2005 | Reily |
| 6,958,077 B2 | 10/2005 | Suddaby |
| 6,966,929 B2 | 11/2005 | Mitchell |
| 6,984,245 B2 | 1/2006 | McGahan et al. |
| 6,986,772 B2 | 1/2006 | Michelson |
| 6,994,727 B2 | 2/2006 | Khandkar et al. |
| 7,025,787 B2 | 4/2006 | Bryan et al. |
| 7,044,971 B2 | 5/2006 | Suddaby |
| 7,052,515 B2 | 5/2006 | Simonson |
| 7,066,960 B1 | 6/2006 | Dickman |
| 7,070,598 B2 | 7/2006 | Lim et al. |
| 7,074,240 B2 | 7/2006 | Pisharodi |
| 7,083,649 B2 | 8/2006 | Zucherman et al. |
| 7,083,650 B2 | 8/2006 | Moskowitz et al. |
| 7,090,698 B2 | 8/2006 | Goble et al. |
| 7,128,761 B2 | 10/2006 | Kuras et al. |
| 7,137,985 B2 | 11/2006 | Jahng |
| 7,147,665 B1 | 12/2006 | Bryan et al. |
| 2001/0005796 A1 | 6/2001 | Zdeblick et al. |
| 2001/0010021 A1 | 7/2001 | Boyd et al. |
| 2001/0016773 A1 | 8/2001 | Serhan et al. |
| 2001/0016774 A1 | 8/2001 | Bresina et al. |
| 2001/0032020 A1 | 10/2001 | Besselink |
| 2001/0034553 A1 | 10/2001 | Michelson |
| 2001/0047207 A1 | 11/2001 | Michelson |
| 2001/0049560 A1 | 12/2001 | Paul et al. |
| 2002/0045943 A1 | 4/2002 | Uk |
| 2002/0049394 A1 | 4/2002 | Roy et al. |
| 2002/0049497 A1 | 4/2002 | Mason |
| 2002/0052656 A1 | 5/2002 | Michelson |
| 2002/0068976 A1 | 6/2002 | Jackson |
| 2002/0068977 A1 | 6/2002 | Jackson |
| 2002/0077702 A1 | 6/2002 | Castro |
| 2002/0095154 A1 | 7/2002 | Atkinson et al. |
| 2002/0095155 A1 | 7/2002 | Michelson |
| 2002/0099444 A1 | 7/2002 | Boyd et al. |
| 2002/0107572 A1 | 8/2002 | Foley et al. |
| 2002/0116065 A1 | 8/2002 | Jackson |
| 2002/0123806 A1 | 9/2002 | Reiley |
| 2002/0128712 A1 | 9/2002 | Michelson |
| 2002/0128713 A1 | 9/2002 | Ferree |
| 2002/0133155 A1 | 9/2002 | Ferree |
| 2002/0138143 A1 | 9/2002 | Grooms et al. |
| 2002/0138146 A1 | 9/2002 | Jackson |
| 2002/0143399 A1 | 10/2002 | Sutcliffe |
| 2002/0151895 A1 | 10/2002 | Soboleski et al. |
| 2002/0151976 A1 | 10/2002 | Foley et al. |
| 2002/0156528 A1 | 10/2002 | Gau |
| 2002/0161366 A1 | 10/2002 | Robie et al. |
| 2002/0169508 A1 | 11/2002 | Songer et al. |
| 2002/0183756 A1 | 12/2002 | Michelson |
| 2003/0004572 A1 | 1/2003 | Goble et al. |
| 2003/0004575 A1 | 1/2003 | Erickson |
| 2003/0009226 A1 | 1/2003 | Graf |
| 2003/0028250 A1 | 2/2003 | Reiley et al. |
| 2003/0040797 A1 | 2/2003 | Fallin et al. |
| 2003/0045939 A1 | 3/2003 | Casutt |
| 2003/0055427 A1 | 3/2003 | Graf |
| 2003/0074068 A1 | 4/2003 | Errico et al. |
| 2003/0078666 A1 | 4/2003 | Ralph et al. |
| 2003/0100949 A1 | 5/2003 | Michelson |
| 2003/0120348 A1 | 6/2003 | Brosnahan et al. |
| 2003/0135278 A1 | 7/2003 | Eckman |
| 2003/0139812 A1 | 7/2003 | Garcia et al. |
| 2003/0139813 A1 | 7/2003 | Messerli et al. |
| 2003/0171813 A1 | 9/2003 | Kiester |
| 2003/0176923 A1 | 9/2003 | Keller et al. |
| 2003/0191532 A1 | 10/2003 | Goble et al. |
| 2003/0199981 A1 | 10/2003 | Ferree |
| 2003/0199982 A1 | 10/2003 | Bryan |
| 2003/0204259 A1 | 10/2003 | Goble et al. |
| 2003/0204260 A1 | 10/2003 | Ferree |
| 2003/0204261 A1 | 10/2003 | Eisermann et al. |
| 2003/0204271 A1 | 10/2003 | Grinberg et al. |
| 2003/0208273 A1 | 11/2003 | Eisermann et al. |
| 2003/0233146 A1 | 12/2003 | Gringberg et al. |
| 2004/0002712 A1 | 1/2004 | Gringberg et al. |
| 2004/0002761 A1 | 1/2004 | Rogers et al. |
| 2004/0002762 A1 | 1/2004 | Hawkins |
| 2004/0006391 A1 | 1/2004 | Reiley |
| 2004/0024462 A1 | 2/2004 | Ferree et al. |
| 2004/0030390 A1 | 2/2004 | Ferree |
| 2004/0030391 A1 | 2/2004 | Ferree |
| 2004/0034430 A1 | 2/2004 | Falahee |
| 2004/0039385 A1 | 2/2004 | Mazda et al. |
| 2004/0039448 A1 | 2/2004 | Pisharodi |
| 2004/0049190 A1 | 3/2004 | Biedermann et al. |
| 2004/0049272 A1 | 3/2004 | Reiley |
| 2004/0049273 A1 | 3/2004 | Reiley |
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049279 A1 | 3/2004 | Sevrain |
| 2004/0049281 A1 | 3/2004 | Reiley |
| 2004/0068318 A1 | 4/2004 | Coates et al. |
| 2004/0073311 A1 | 4/2004 | Ferree |
| 2004/0097931 A1 | 5/2004 | Mitchell |
| 2004/0098131 A1 | 5/2004 | Bryan et al. |
| 2004/0102848 A1 | 5/2004 | Michelson |
| 2004/0111161 A1 | 6/2004 | Trieu |
| 2004/0126407 A1 | 7/2004 | Falahee |
| 2004/0127991 A1 | 7/2004 | Ferree |
| 2004/0133281 A1 | 7/2004 | Khandkar et al. |
| 2004/0138749 A1 | 7/2004 | Zucherman et al. |
| 2004/0143270 A1 | 7/2004 | Zucherman et al. |
| 2004/0143332 A1 | 7/2004 | Krueger et al. |
| 2004/0162562 A1 | 8/2004 | Martz |
| 2004/0162618 A1 | 8/2004 | Mujwid et al. |
| 2004/0176764 A1 | 9/2004 | Dant |
| 2004/0176845 A1 | 9/2004 | Zubok et al. |
| 2004/0176850 A1 | 9/2004 | Zubok et al. |
| 2004/0181284 A1 | 9/2004 | Simonson |
| 2004/0181285 A1 | 9/2004 | Simonson |
| 2004/0186570 A1 | 9/2004 | Rapp |
| 2004/0186576 A1 | 9/2004 | Biscup et al. |
| 2004/0186577 A1 | 9/2004 | Ferree |
| 2004/0193272 A1 | 9/2004 | Zubok et al. |
| 2004/0220567 A1 | 11/2004 | Eisermann et al. |
| 2004/0220670 A1 | 11/2004 | Eisermann et al. |
| 2004/0220672 A1 | 11/2004 | Shadduck |
| 2004/0230307 A1 | 11/2004 | Eisermann |
| 2004/0243240 A1 | 12/2004 | Beaurain et al. |
| 2004/0243241 A1 | 12/2004 | Istephanous et al. |
| 2004/0249461 A1 | 12/2004 | Ferree |
| 2004/0249462 A1 | 12/2004 | Huang |
| 2004/0254643 A1 | 12/2004 | Jackson |
| 2005/0027359 A1 | 2/2005 | Mashburn |
| 2005/0033432 A1 | 2/2005 | Gordon et al. |

(56) References Cited

U.S. PATENT DOCUMENTS

| | | |
|---|---|---|
| 2005/0033439 A1 | 2/2005 | Gordon et al. |
| 2005/0043800 A1 | 2/2005 | Paul et al. |
| 2005/0043802 A1 | 2/2005 | Eisermann et al. |
| 2005/0055099 A1 | 3/2005 | Ku |
| 2005/0071008 A1 | 3/2005 | Kirschman |
| 2005/0075644 A1 | 4/2005 | Dipoto et al. |
| 2005/0080488 A1 | 4/2005 | Schultz |
| 2005/0113916 A1 | 5/2005 | Branch, Jr. |
| 2005/0113920 A1 | 5/2005 | Foley et al. |
| 2005/0119747 A1 | 6/2005 | Fabris Monterumici et al. |
| 2005/0119753 A1 | 6/2005 | McGahan et al. |
| 2005/0131540 A1 | 6/2005 | Trieu |
| 2005/0143820 A1 | 6/2005 | Zucherman et al. |
| 2005/0149189 A1 | 7/2005 | Mokhtar et al. |
| 2005/0149196 A1 | 7/2005 | Zucherman et al. |
| 2005/0154461 A1 | 7/2005 | Humphreys et al. |
| 2005/0154462 A1 | 7/2005 | Zucherman et al. |
| 2005/0154464 A1 | 7/2005 | Humphreys et al. |
| 2005/0154465 A1 | 7/2005 | Hodges et al. |
| 2005/0154466 A1 | 7/2005 | Humphreys et al. |
| 2005/0154467 A1 | 7/2005 | Peterman et al. |
| 2005/0159818 A1 | 7/2005 | Blain |
| 2005/0165407 A1 | 7/2005 | Diaz |
| 2005/0165484 A1 | 7/2005 | Ferree |
| 2005/0171608 A1 | 8/2005 | Peterman et al. |
| 2005/0171609 A1 | 8/2005 | Humphreys et al. |
| 2005/0171610 A1 | 8/2005 | Humphreys et al. |
| 2005/0187625 A1 | 8/2005 | Wolek et al. |
| 2005/0192671 A1 | 9/2005 | Bao et al. |
| 2005/0197702 A1 | 9/2005 | Coppes et al. |
| 2005/0209698 A1 | 9/2005 | Gordon et al. |
| 2005/0216081 A1 | 9/2005 | Taylor |
| 2005/0228500 A1 | 10/2005 | Kim et al. |
| 2005/0234551 A1 | 10/2005 | Fallin et al. |
| 2005/0234555 A1 | 10/2005 | Sutton et al. |
| 2005/0240270 A1 | 10/2005 | Zubock et al. |
| 2005/0251261 A1 | 11/2005 | Peterman |
| 2005/0256578 A1 | 11/2005 | Blatt et al. |
| 2005/0261773 A1 | 11/2005 | Ferree |
| 2005/0261774 A1 | 11/2005 | Trieu |
| 2005/0267581 A1 | 12/2005 | Marnay et al. |
| 2005/0273178 A1 | 12/2005 | Boyan et al. |
| 2005/0277930 A1 | 12/2005 | Parsons |
| 2005/0277938 A1 | 12/2005 | Parsons |
| 2005/0283237 A1 | 12/2005 | Zucherman et al. |
| 2005/0283242 A1 | 12/2005 | Zucherman et al. |
| 2006/0004448 A1 | 1/2006 | Casey |
| 2006/0009849 A1 | 1/2006 | Reiley |
| 2006/0025862 A1 | 2/2006 | Villiers et al. |
| 2006/0036325 A1 | 2/2006 | Paul et al. |
| 2006/0064170 A1 | 3/2006 | Smith et al. |
| 2006/0069437 A1 | 3/2006 | Weber |
| 2006/0069438 A1 | 3/2006 | Zucherman et al. |
| 2006/0069440 A1 | 3/2006 | Zucherman et al. |
| 2006/0085076 A1 | 4/2006 | Krishna et al. |
| 2006/0089717 A1 | 4/2006 | Krishna et al. |
| 2006/0095133 A1 | 5/2006 | Eisermann et al. |
| 2006/0106459 A1 | 5/2006 | Truckai et al. |
| 2006/0116768 A1 | 6/2006 | Krueger et al. |
| 2006/0129160 A1 | 6/2006 | Liu |
| 2006/0142860 A1 | 6/2006 | Navarro et al. |
| 2006/0178744 A1 | 8/2006 | De et al. |
| 2006/0178745 A1 | 8/2006 | Bartish, Jr. et al. |
| 2006/0241769 A1 | 10/2006 | Gordon et al. |
| 2006/0241771 A1 | 10/2006 | Gordon et al. |
| 2006/0247650 A1 | 11/2006 | Yerby et al. |
| 2006/0247769 A1 | 11/2006 | Molz et al. |
| 2007/0050033 A1 | 3/2007 | Reo |
| 2007/0050037 A1 | 3/2007 | Snell et al. |
| 2007/0055378 A1 | 3/2007 | Ankney et al. |
| 2007/0123884 A1* | 5/2007 | Abdou ............... A61B 17/7059 606/279 |
| 2007/0270972 A1* | 11/2007 | Gordon ................ A61B 17/746 606/257 |
| 2010/0298938 A1* | 11/2010 | Humphreys .......... A61F 2/4405 623/17.11 |

FOREIGN PATENT DOCUMENTS

| | | |
|---|---|---|
| CN | 1713866 A | 12/2005 |
| CN | 1917832 A | 2/2007 |
| DE | 2804936 A1 | 8/1979 |
| DE | 3023353 A1 | 4/1983 |
| DE | 0277282 A1 | 10/1998 |
| DE | 20017962 U1 | 1/2001 |
| DE | 10135771 A1 | 2/2003 |
| DE | 202004015198 U1 | 11/2004 |
| EP | 0042271 A1 | 9/1984 |
| EP | 0640326 A1 | 3/1995 |
| EP | 0677277 A2 | 10/1995 |
| EP | 0716840 A2 | 6/1996 |
| EP | 0953317 A1 | 11/1999 |
| EP | 1281361 A1 | 2/2003 |
| EP | 0820731 B1 | 5/2003 |
| EP | 0886506 B1 | 4/2005 |
| EP | 1685811 A1 | 8/2006 |
| EP | 1711134 A1 | 10/2006 |
| EP | 1711137 A2 | 10/2006 |
| EP | 1711141 B1 | 10/2006 |
| FR | 2676911 A1 | 12/1992 |
| FR | 2724108 A1 | 9/1994 |
| FR | 2718635 A1 | 10/1995 |
| FR | 2742653 A1 | 12/1995 |
| FR | 2723841 A1 | 3/1996 |
| FR | 2799638 A1 | 4/2001 |
| JP | 63145650 A | 6/1988 |
| JP | 2261446 A | 10/1990 |
| JP | 10501705 A | 2/1998 |
| JP | 10286262 A | 10/1998 |
| JP | 2001511392 A | 8/2001 |
| JP | 2002512079 A | 4/2002 |
| JP | 2002521090 A | 7/2002 |
| JP | 2002528223 A | 9/2002 |
| JP | 2002532142 A | 10/2002 |
| JP | 2003512090 A | 4/2003 |
| JP | 2003515381 A | 5/2003 |
| JP | 2003518978 A | 6/2003 |
| JP | 2004514498 A | 5/2004 |
| JP | 2004167254 A | 6/2004 |
| JP | 2005503861 A | 2/2005 |
| JP | 2005515002 A | 5/2005 |
| JP | 2005526550 A | 9/2005 |
| JP | 2006500078 A | 1/2006 |
| JP | 2006502274 A | 1/2006 |
| WO | 1993010725 A2 | 6/1993 |
| WO | 1996000049 A1 | 1/1996 |
| WO | 1997035529 A1 | 10/1997 |
| WO | 1998014142 A1 | 4/1998 |
| WO | 1999008627 A1 | 2/1999 |
| WO | 1999053871 A1 | 10/1999 |
| WO | 2000004851 A1 | 2/2000 |
| WO | 2000041654 A2 | 7/2000 |
| WO | 2000069351 A1 | 11/2000 |
| WO | 2001039678 A1 | 6/2001 |
| WO | 2001045576 A1 | 6/2001 |
| WO | 2002011650 A2 | 2/2002 |
| WO | 2002043603 A1 | 6/2002 |
| WO | 2002047586 A1 | 6/2002 |
| WO | 2003026522 A2 | 4/2003 |
| WO | 2003041618 A2 | 5/2003 |
| WO | 2003045262 A2 | 6/2003 |
| WO | 2003059212 A1 | 7/2003 |
| WO | 2003084449 A1 | 10/2003 |
| WO | 2003101350 A1 | 4/2004 |
| WO | 2004034935 A1 | 4/2004 |
| WO | 2004041131 A2 | 5/2004 |
| WO | 2004098465 A1 | 11/2004 |
| WO | 2005011522 A2 | 2/2005 |
| WO | 2005025431 A | 3/2005 |

(56) References Cited

FOREIGN PATENT DOCUMENTS

| WO | 2005070354 A2 | 4/2005 |
|---|---|---|
| WO | 2005067824 A1 | 7/2005 |
| WO | 2005070278 A2 | 8/2005 |
| WO | 2005070349 A1 | 8/2005 |
| WO | 2005070350 A2 | 8/2005 |
| WO | 2005070352 A2 | 8/2005 |
| WO | 2005070353 A1 | 8/2005 |
| WO | 2005077304 A1 | 8/2005 |
| WO | 2005094736 A1 | 10/2005 |
| WO | 2005112835 A2 | 12/2005 |
| WO | 2005117725 A2 | 12/2005 |
| WO | 2006063354 A1 | 6/2006 |
| WO | 2007028098 A2 | 3/2007 |
| WO | 2007087477 A1 | 8/2007 |
| WO | 2007124467 A2 | 11/2007 |

OTHER PUBLICATIONS

PCT—International Searching Authority, International Search Report and Written Opinion of the International Searching Authority for PCT/US2005/000705, dated Jun. 6, 2005, 17 pages.

PCT—European Patent Office, International Search Report and International Preliminary Examination Report for PCT/US2001/024791, dated Jun. 20, 2002, 8 pages.

PCT—International Searching Authority, International Search Report and Written Opinion of the International Searching Authority for Application No. PCT/US2005/000586, dated Dec. 16, 2005, 17 pages.

PCT—International Searching Authority, International Search Report and Written Opinion of the International Searching Authority for PCT/US2005/000706, dated Sep. 13, 2005, 19 pages.

PCT—International Searching Authority, International Search Report and Written Opinion of the International Searching Authority for PCT/US2007/060491, dated Apr. 25, 2007, 8 pages.

PCT—International Searching Authority, International Search Report and Written Opinion of the International Searching Authority for Application No. PCT/US2005/000656, dated Aug. 23, 2005, 12 pages.

PCT—International Searching Authority, International Search Report and Written Opinion of the International Searching Authority for Application No. PCT/US2005/000704, dated Aug. 23, 2005, 17 pages.

PCT—International Searching Authority, International Search Report and Written Opinion of the International Searching Authority for Application No. PCT/US2005/000585, dated Jun. 8, 2005, 12 pages.

TH. Marnay—Orthopedic Surgeon, Lumbar Intervertebral Arthroplasty—Jun.-Sep. 1991, 15 pages, Kennedy Clinic, U.S.A. (See French article in line item 11).

TH. Marnay—La Revue De Medecine Orthopedique, L'Arthoplatie Intervertebral Lombaire, No. 25, Jun.-Sep. 1991, 9 pages, Kennedy Clinic, France (same article as line item 10).

AB Swanson, et al.—The Journal of Bone and Joint Surgery, Unicompartmental and Biocompartmental Arthroplasty of the Knee with a Finned Metal Tibial-Plateau Implant, Oct. 1985, 9 pages, J Bone Joint Surg Am. 1985;67:1175-1182, Needham, MA.

David S. Hungerford, M.D., Kenneth A. Krackow, M.D., Robert V. Kenna—Total Knee Arthroplasty: A Comprehensive Approach, 1984, 20 pages, Publisher Williams and Wilkins, Baltimore, MD.

David S. Hungerford, M.D., and Robert V. Kenna—Preliminary Experience with a Total Knee Prosthesis with Pourous Coating Used Without Cement, Jun. 1983, 13 pages, J.B.Lippincott, Co., No. 176, U.S.A.

T. Hoogland, A.D. Steffe, J.D. Black, A.S. Greenwald—Total Lumbar Intervertebral Disc Replacement: Testing of a New Articulating Spacer in Human Cadaver Spines, Feb. 21-23, 1978, 1 page, Cleveland Clinic Foundation, 24th Annual ORS, Dallas, TX.

Jeanette E. Ahrens, PHD, Alexis P Shelokov, MD, Jeffrey L. Carver, BS—Normal Joint Mobility is Maintained with an Artificial Disc Prosthesis, 1999, Texas Health Research Institute, Plano, Texas.

Zimmer—The Journal of Bone and Joint Surgery, Jul. 1970, 2 pages, American Volume, vol. 52-A, No. 5, Boston, MA.

Viscoglioski Bro., LLC, Spine Arthroplasty: Market Potential & Technology Update, Spine Industry Analysis Series, Nov. 2001, 202 pages, U.S.A.

A.H. Crenshaw—Campbell's Operative Orthopedics, 1987, 11 pages, Seventh Edition, vol. 2, The C.V. Mosby Company, 1987.

Zimmer—The Journal of Bone and Joint Surgery, Sep. 1971, 2 pages, American Volume, vol. 53-A, No. 6, Boston, MA.

International Search Authority, European Patent Office, International Search Report and Written Opinion for PCT Appl. No. PCT/US2008/065504, dated Dec. 1, 2009, 1-11 pgs.

Australian Patent Office, Patent Examination Report No. 1 for Pat. Appl. 2008259888, dated Sep. 28, 2012, 1-4 pgs.

European Patent Office, European Search Report for Pat. Appl. No. 18787514.1, dated Dec. 23, 2020, pp. 1-8.

International Search Authority, United States Patent & Trademark Office, International Search Report and Written Opinion for PCT Appl. No. PCT/US2018/028028, dated Jun. 27, 2018, pp. 1-8.

* cited by examiner

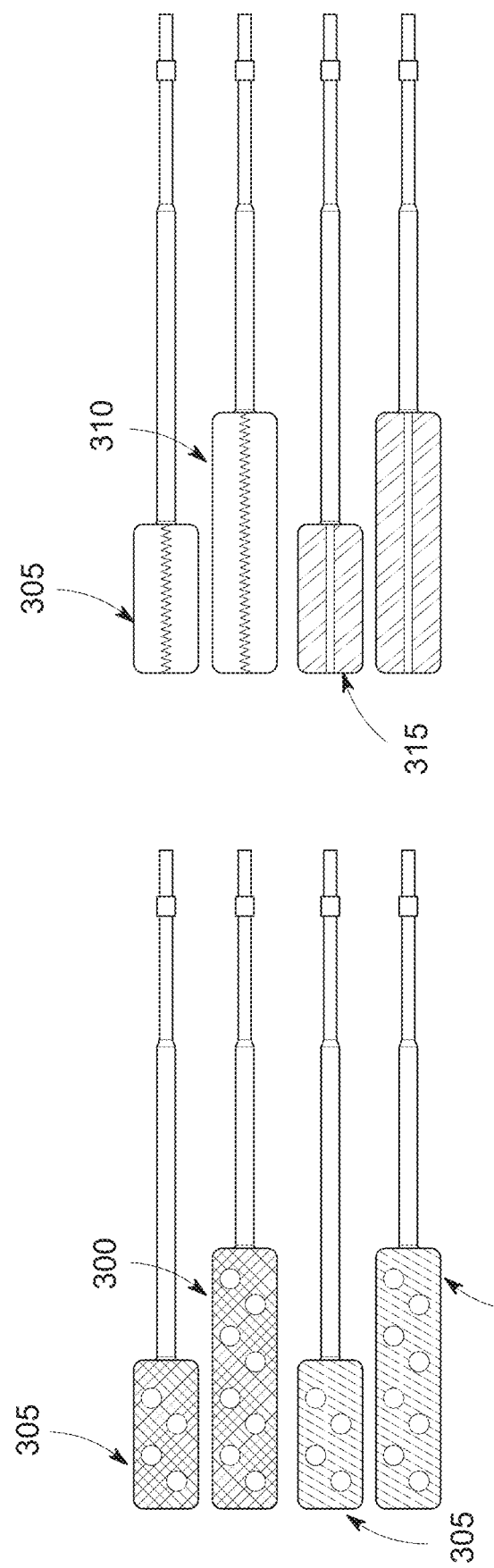

SPINAL OSTEOTOMY

CROSS-REFERENCE TO RELATED APPLICATIONS

This application is a continuation of, and claims priority to, U.S. application Ser. No. 15/955,611, filed on Apr. 17, 2018, which is a continuation-in-part of U.S. application Ser. No. 15/712,046, filed on Sep. 21, 2017, which is a continuation of U.S. application Ser. No. 14/486,065, filed on Sep. 15, 2014, which in turn is a divisional application of U.S. application Ser. No. 11/839,821, filed on Aug. 16, 2007, which claims priority from U.S. application Ser. No. 11/757,084, filed on Jun. 1, 2007, the disclosures of which are each incorporated herein by reference. This application further claims the benefit, through U.S. application Ser. No. 15/955,611, of U.S. Provisional Patent Application Ser. No. 62/486,329 entitled "HHALL Osteotomy," filed Apr. 17, 2017, and U.S. Provisional Patent Application Ser. No. 62/654,963 entitled "Spinal Osteotomy," filed Apr. 9, 2018, the disclosures of which are each incorporated by reference herein in their entireties.

TECHNICAL FIELD

The present invention relates generally to devices, methods, systems and techniques for repairing and/or stabilizing the spine and/or other bones of a patient during spinal surgery.

BACKGROUND

At times, the source of a patient's back pain may not be clear. Among possible causes for such pain are disease, degradation and/or injury to the spinal bones and/or discs of the spine, as well as to various ancillary structures such as the lamina and/or associated facet joints. While spinal fusion and/or disc arthroplasty procedures have been successful in treating spinal joints to reduce pain, such treatments are often limited in their efficacy, often fuse or immobilize portions or a patient's spine, and are often unable to address and/or correct severe spinal deformities, including spinal dislocations and/or curvature abnormalities such as juvenile and/or adult scoliosis. Therefore, a motion preserving joint replacement system is needed that can reduce and/or correct severe spinal deformities while replacing all or part of the function of the spinal disc and/or associated spinal structures.

SUMMARY OF THE INVENTION

In various embodiments, surgical methods and techniques are described wherein portions of a patient's spinal bones may be shaped, shaved, resected and/or removed, including portions of a vertebral endplate and/or pedicular portion(s) (and/or associated structures), with at least one or more portions of the pedicle retained to provide at least partial support for a prosthetic system that is implanted between the upper and lower vertebrae.

In various embodiments, the prosthetic system can comprise an upper joint component and a lower joint component. The upper joint component can comprise an upper contact surface and an upper articulation surface, and the lower joint component can comprise a lower contact surface and a lower articulation surface configured to movably engage the upper articulation surface to form an articulating joint. The articulating joint is adapted for implantation within a disc space between the upper and lower vertebrae, allowing the upper and lower vertebrae to move relative to one another. The lower joint component will also desirably include a support or bridge component extending posteriorly from the disc space, with at least a portion of the bridge component including an outer surface which abuts and/or engages with at least a portion of a pedicle and/or portions of the vertebral arch.

In another embodiment, a prosthetic system for implantation between upper and lower vertebrae comprises an upper joint component having an upper contact surface and an upper articulation surface. The system further has a lower joint component comprising a lower contact surface and a lower articulation surface configured to movably engage the upper articulation surface to form an articulating joint. The articulating joint is configured for implantation within a disc space between the upper and lower vertebrae, allowing the upper and lower vertebrae to move relative to one another. The lower joint component can further include a posterior support which extends from a posterior aspect of the lower joint component, the posterior support including at least one fixation element for securing the lower joint component to the lower vertebrae.

In still another embodiment, a surgical method comprises non-invasively imaging at least upper and lower vertebral bodies of a patient's spine, and then preoperatively planning the surgical removal of some portions of an endplate and one or more pedicles of the lower vertebral body to alter, restore and/or correct the alignment between the upper and lower vertebral bodies to a desired and/or more anatomically correct alignment. Surgical removal according to the preoperative plan can be accomplished, which can include removal of the endplate and/or a portion of one or more pedicles of the lower vertebral body, and then insertion of a prosthetic system between the upper and lower vertebrae, wherein the system comprises an upper joint component and a lower joint component, with the lower joint component including a support extending posteriorly from the lower joint component, the posterior support including a surface adapted and configured to fit within at least a remaining portion of one or more pedicles of the lower vertebral body.

In the various embodiments described herein the planning and surgical corrections to the spinal alignment can include alterations to the lordotic curvature of the patient's spine, alterations to the lateral curvature of the patient's spine (i.e., to address scoliosis, for example), and/or various combinations thereof. If desired, a surgical correction to a specific region of the spine may result in a more-normal anatomical alignment of the affected segment, or the surgical correction may result in an alignment that is further away from the natural alignment (such as where the treated segment desirably compensates for other misaligned levels that may not be surgically treated). In various embodiments, the anatomical imaging, analysis, approach, vertebral preparation, implant preparation and/or placement can be accomplished with the aid of surgical navigation and/or robotic guidance. Due to the complex nature of the preoperative planning and/or execution, these tools may be particularly well suited for the present invention to allow execution of the plan in the operative environment.

BRIEF DESCRIPTION OF THE DRAWINGS

The foregoing and other objects, aspects, uses, features, and advantages of embodiments will become more apparent and may be better understood by referring to the following detailed description of the preferred embodiments, taken in conjunction with the accompanying drawings, wherein:

FIG. 18 depicts a top plan view of various rasps and alignment tools for use in preparing spinal anatomy;

DETAILED DESCRIPTION

Figure 1:
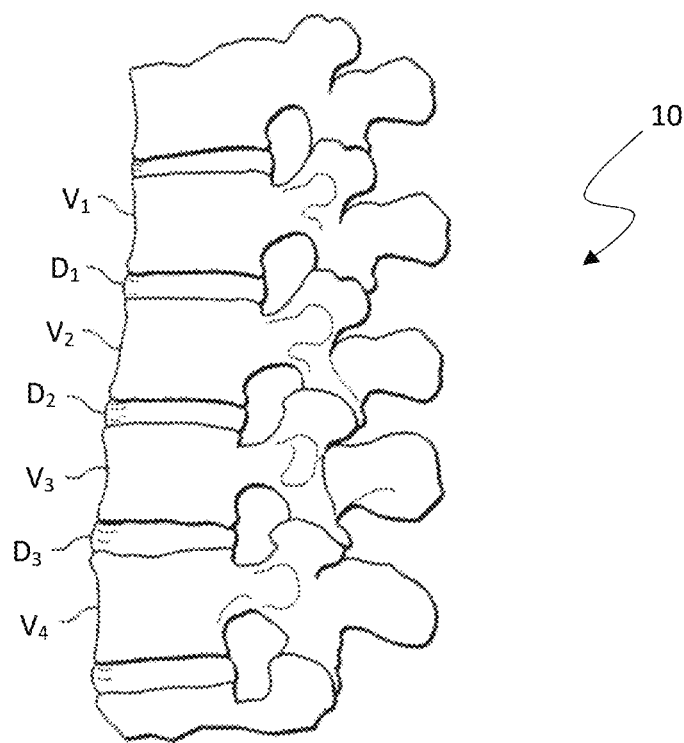
FIG. 1 depicts a sagittal view of the lumbar spinal region of a healthy, human spinal column.

Various features of the present invention include the recognition of a need for a more effective and versatile system of addressing spinal disease and deformities, including the correction and/or alteration of spinal levels using a motion preserving construct. A variety of configurations, sizes and shapes of such components and associated tools can be utilized in diverse anatomical regions, including use in spinal surgery as well as other anatomical locations. In various medical applications, the disclosed components and related surgical tools and techniques can desirably facilitate the treatment of various types of bone disease and/or damage by surgeons, which can be important to achieve the most accurate and best implant performance and/or fit, as well as facilitate patient recovery.

This specification describes novel systems, devices and methods to treat spinal fractures. Aspects of the present invention will be described with regard to the treatment of vertebral bodies at the lumbar and/or thoracic levels. It should be appreciated, however, that various aspects of the present invention may not limited in their application to thoracic or lumbar injuries. The systems and methods may be applicable to the treatment of fractures in diverse bone types. Embodiments will now be described with reference to the drawings, wherein like reference numerals are used to refer to like elements throughout. It should be understood that the figures are not necessarily to scale.

The present disclosure relates generally to systems and methods for spinal surgery and, more particularly in some embodiments, to spinal arthroplasty systems and methods for posterior implantation. For the purposes of promoting an understanding of the principles of the invention, reference will now be made to embodiments or examples illustrated in the drawings, and specific language will be used to describe the same. It will nevertheless be understood that no limitation of the scope of the invention is thereby intended. Any alteration and further modifications in the described embodiments, and any further applications of the principles of the invention as described herein are contemplated as would normally occur to one skilled in the art to which the disclosure relates.

Referring first to FIG. 1, a sagittal view of a vertebral column 10 is shown, illustrating a sequence of vertebrae V1, V2, V3, V4 separated by natural intervertebral discs D1, D2, D3, respectively. Although the illustration generally depicts a lumbar section of a spinal column, it is understood that the devices, systems, and methods of this disclosure may also be applied to all regions of the vertebral column, including thoracic and cervical regions.

Figure 2:
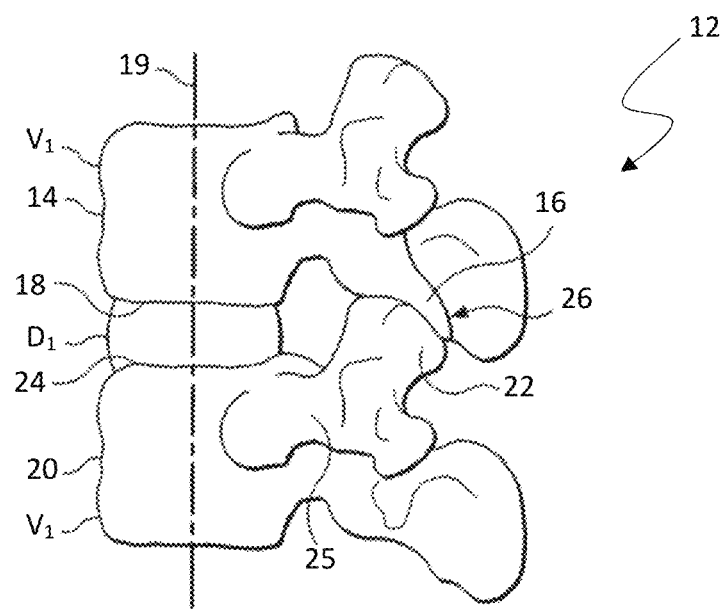
FIG. 2 depicts a sagittal view of a single spinal joint.

Referring now to FIG. 2, a vertebral joint 12 of the vertebral column 10 includes the adjacent vertebrae V1, V2 between which the intervertebral disc D1 extends. The vertebra V1 includes a generally cylindrical vertebral body portion 14, an inferior articular process 16, and an inferior endplate 18. The vertebra V2 includes a generally cylindrical vertebral body portion 20, a superior articular process 22, and a superior endplate 24. For reference purposes, a longitudinal axis 19 extends through the centers of the cylindrical vertebral body portions 14, 20. A pedicle 25 extends between the vertebral body portion 20 and superior articular process 22. The inferior articular process 16 and the superior articular process 22 form a facet or zygapophyseal joint 26. The facet joint 26 has a fluid filled capsule and cartilage to provide articulating surfaces for the articular processes 16, 22. Both the disc D1 and the facet joint 26 permit motion between adjacent bone surfaces, allowing the total vertebral joint 12 a normal range of flexion/extension, lateral bending, and rotational motion. As the disc D1 and/or the facet joint 26 deteriorate due to aging, injury, disease, or other factors, all or portions of the disc, the facet joint, and/or the articular processes 16, 22 may be removed and replaced by a prosthetic device which may preserve motion in the spinal joint 12. Although not described in detail, a second bilateral prosthetic device may also be used to replace a portion of the function of disc D1 and/or the function of a second facet joint opposite the facet joint 26.

Figure 3A:
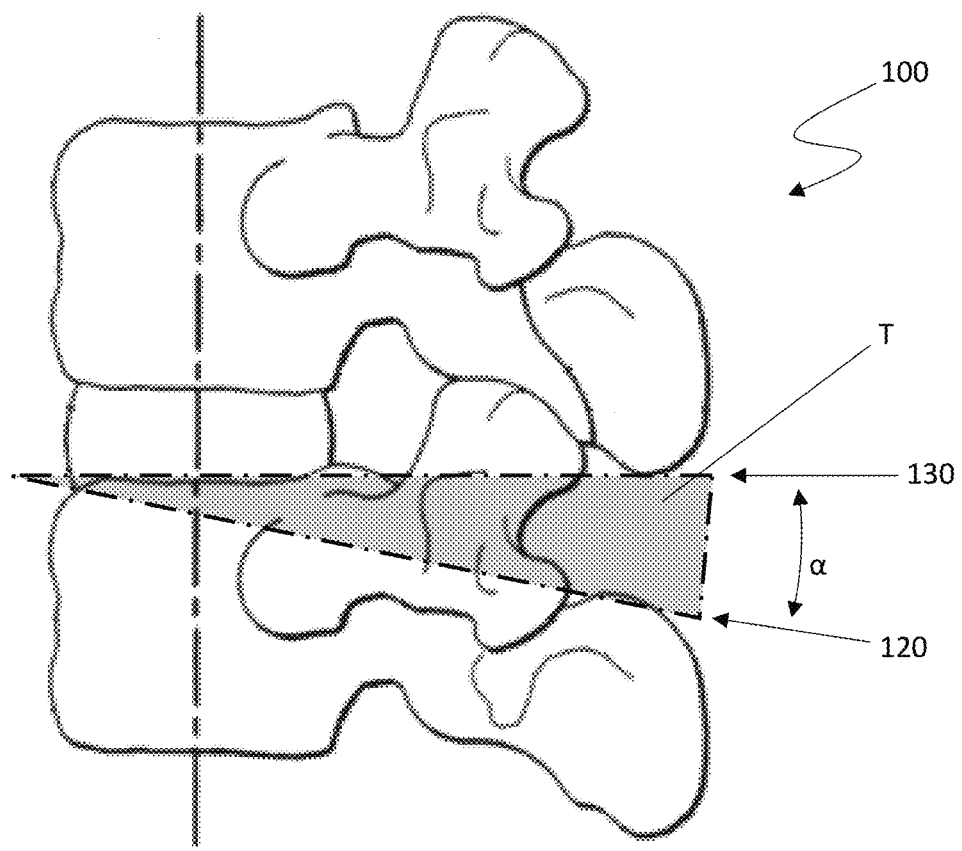
FIG. 3A is lateral view of one exemplary embodiment of a surgical technique for altering the alignment of a functional spinal unit.

FIG. 3A depicts a side view of one exemplary spinal motion unit 100 that is undergoing a surgical procedure in accordance with one exemplary embodiment of the present invention. In this embodiment, preoperative image data of the spinal motion unit has been obtained, and a surgical plan to alter the alignment of the spinal motion has being proposed. In this embodiment, a proposed lower component alignment path 120 has been presented, which will desirably result in the surgical removal of a "wedge" of bony material from the lower vertebral body 105 and/or one or both pedicles 110, which is represented by the shaded triangle "T" of FIG. 3A (involving removal of bony material at or below the anatomical alignment line 130 up to the revised alignment line of 120). Desirably, this surgical plan will allow some and/or all of at least the bottom of the pedicles to be preserved during such removal, such that the remaining portions of the pedicle are attached to the vertebral body, to provide additional stability to lower surfaces of the implant. If desired, the resection may be symmetrical on each side of the vertebral body, or the resection may be asymmetrical in some fashion.

In various embodiments, the use of robotics and/or computer guided surgical platforms (and/or computer-aided navigation) are contemplated herein, including in the planning and/or execution stages of the surgery.

Figure 3B:
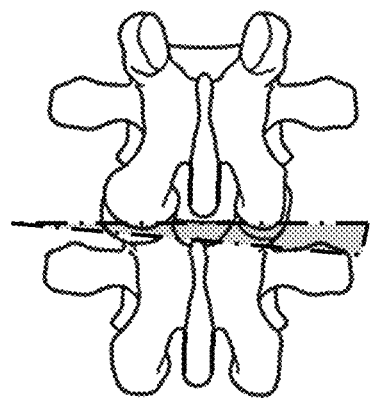
FIG. 3B is a posterior view of another exemplary embodiment of a surgical technique for altering the alignment of a functional spinal unit.

FIG. 3B depicts a posterior view of the exemplary spinal motion unit 100, where an asymmetrical resection is being planned to desirably correct an undesirable medial/lateral curvature of the spine. In this embodiment, more material will be resected from right side of the spinal motion unit than from the left side, which will desirably induce a slight medial curvature to the patient's spine (i.e., providing a desired coronal plan correction). In addition, as previously noted, the surgical plan will desirably allow some and/or all of at least the bottom of the pedicles to be preserved during such removal, such that the remaining portions of the pedicle are attached to the vertebral body, to provide additional stability to lower surfaces of the implant.

Figure 3C:
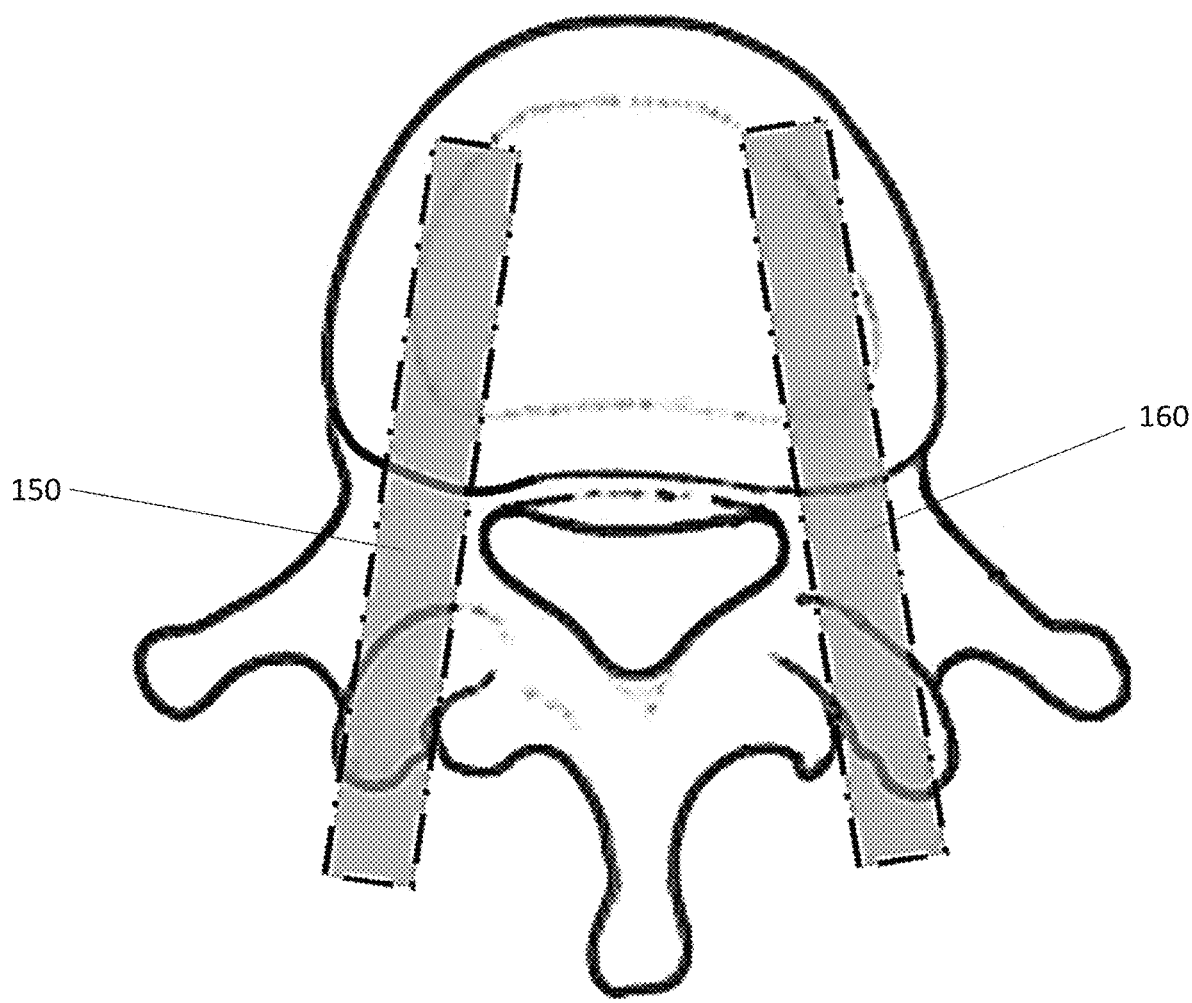
FIG. 3C is a superior view of a surgical technique for altering the alignment of a functional spinal unit.

FIG. 3C depicts a top view of a vertebral body of the surgical plan on FIG. 3A, in which the proposed bone "wedges" are shown in shadow as planning boxes 150 and 160. In this embodiment, the wedges could be taken from both sides for sagittal correction, or both side asymmetrically or unilaterally for combined coronal and sagittal correction.

Figure 4A:
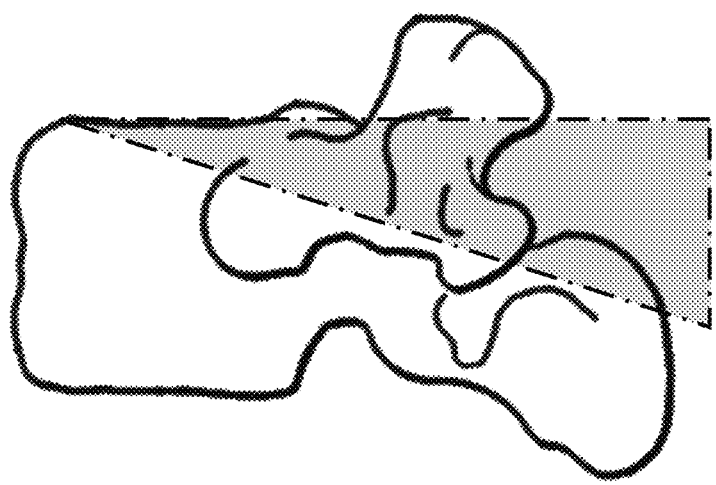
FIGS. 4A through 4D depicts exemplary planning steps for altering and/or correcting the lordotic alignment of a functional spinal unit.
Figure 4B:
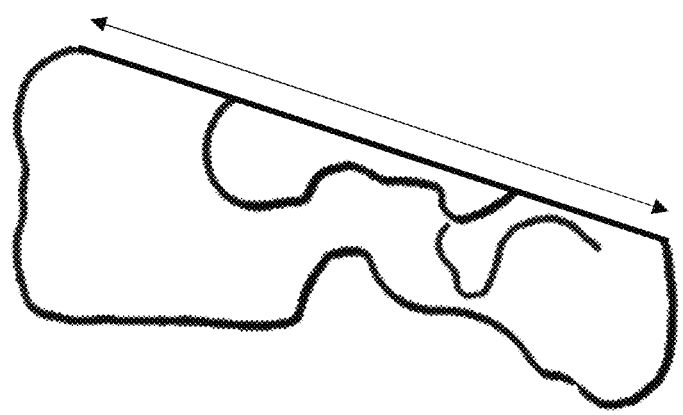
Figure 4C:
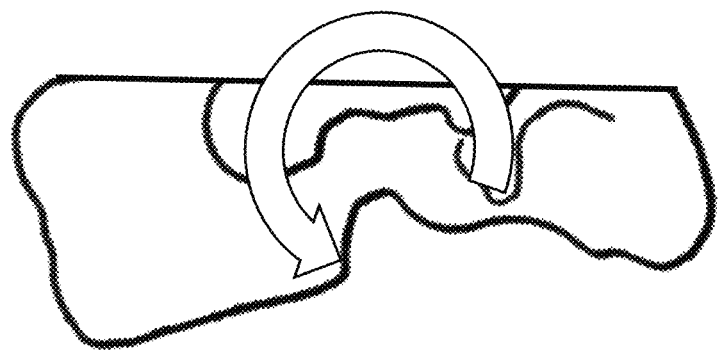
Figure 4D:
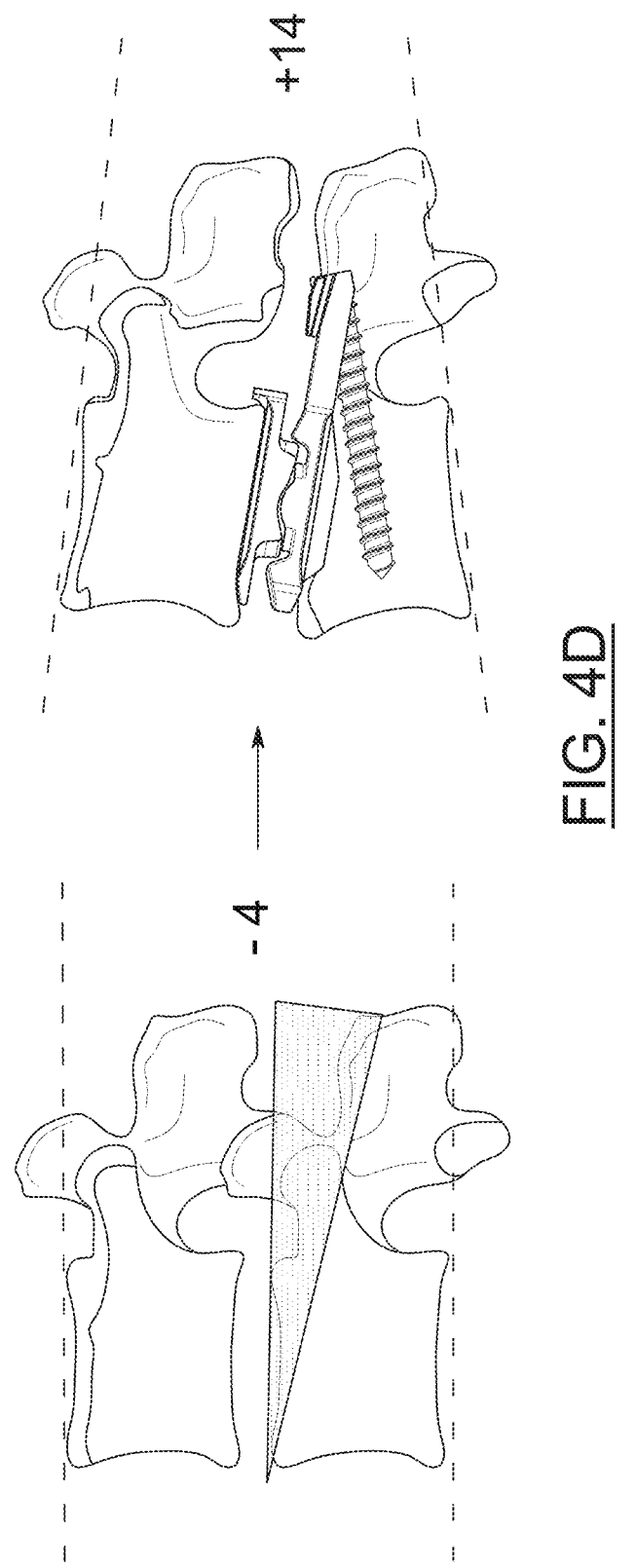
Figure 5:
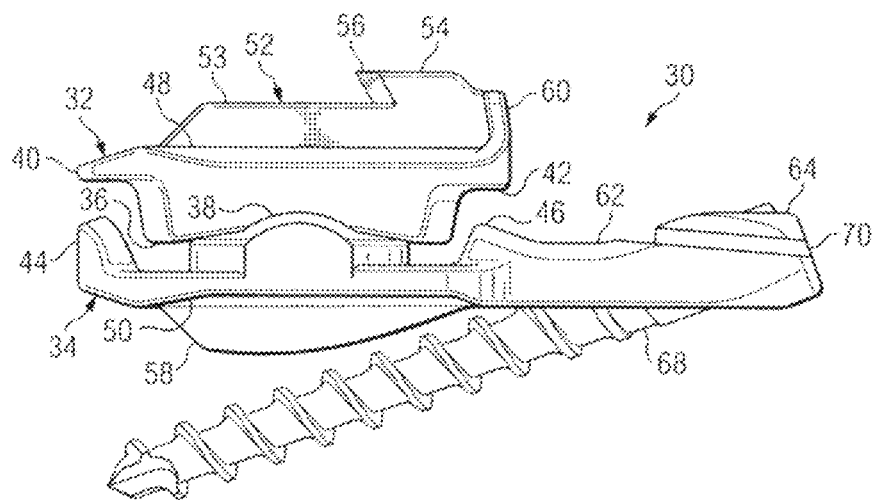
FIGS. 5 through 9 depict one exemplary embodiment of a prosthetic device which allows for significant resection of a vertebral body and/or pedicle and associated spinal structures, while preserving spinal stability and motion.
Figure 6:
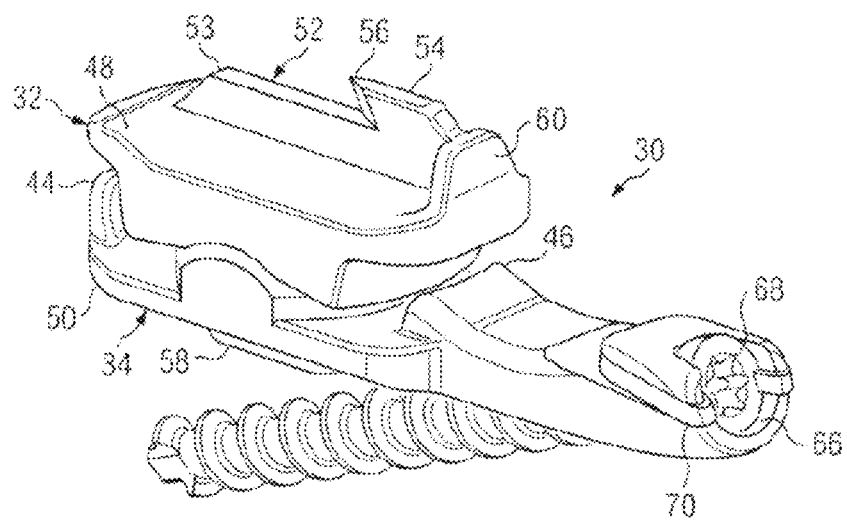
Figure 7:
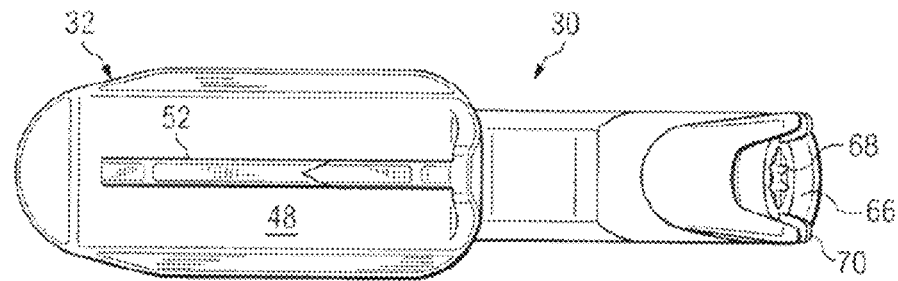
Figure 8:
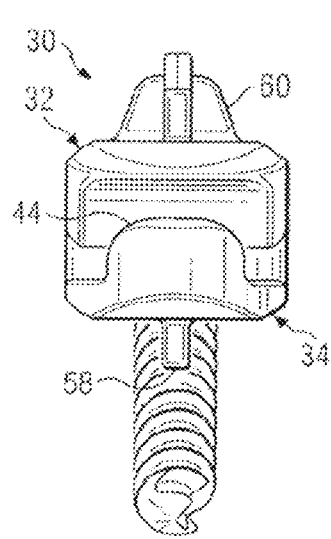
Figure 9:
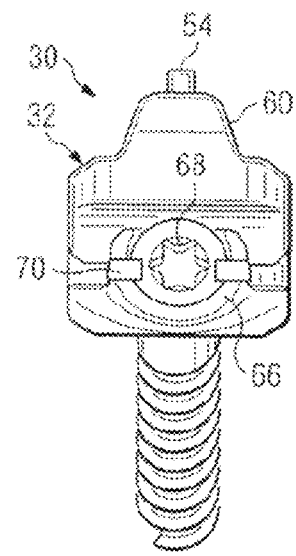

FIGS. 4A through 4D depict one exemplary lordotic correction that could be obtained using the teachings of the present invention. In this embodiment, a vertebral body 200 is imaged, and a surgical resection plan is proposed (indicated as the shaded triangle). FIG. 4B shows the vertebral body 200 after resection, and FIG. 4C depicts the new orientation of the vertebral body 200 after resection is complete, which could represent an increased lordotic curvature of the lumbar spine when accomplished at the lumbar level. FIG. 4D depicts the resulting correction to the functional spinal unit, wherein a negative 4 degree curvature was altered and stabilized to a positive 14 degree curvature using the techniques and implants described herein.

Referring now to FIGS. 5 through 9, in one embodiment, a prosthetic device 30 can be provided that allows for significant resection of a vertebral body and/or pedicle (including resection and/or preparation of only part of a pedicle) and associated spinal structures, while still preserving stability and/or motion in the spinal joint. The prosthetic device 30 can include an upper joint component 32 and a lower joint component 34. The upper joint component 32 desirably includes an articulation surface 36, which may be smooth, concave, and/or generally spherical in shape. The lower joint component 34 can include an articulation surface 38, which may be smooth, convex, and/or generally spherical in shape. As assembled, the articulation surface 36 may engage the articulation surface 38 to produce a ball-and-socket style anterior joint.

As defined herein, a "spherical" shaped surface could include any curved surface having a uniform radius of curvature and may refer to a spherical cap or a segment of a sphere. In various alternative embodiments, non-spherical curved surfaces may function as articulation surfaces to impart specific limits to the range of motion of the prosthetic device. In still another alternative embodiment, the joint may be inverted with the upper articulation surface having a convex shape and the lower articulation surface having a concave articulation surface The upper joint component 32 may further include bumpers or motion limiters 40, 42 which in this embodiment are depicted as recessed shoulders. The lower joint component 34 can also include bumpers or motion limiters 44, 46 which in this embodiment are upwardly protruding extensions, spaced apart from the articulation surface 38. As will be described in greater detail below, the pair of motion limiters 40, 44 and the pair of motion limiters 42, 46 may serve to constrain flexion/extension motion to a desirable range, preventing or limiting the dislocation of the joint formed by the articulation surfaces 36, 38. The motion limiters may be shaped to provide a greater or lesser range of flexion/extension motion. For example, a surface on the motion limiter 44 angled away from the articulation surface 38 may permit greater flexion motion than would a motion limiter surface parallel to an axis of the spine.

The upper joint component 32 may further include an outer contact surface 48 for interfacing with the vertebral endplate 18, and the lower joint component 34 may include an outer contact surface 50 for interfacing with the vertebral endplate 24.

The upper joint component 32 may further include an upper keel 52 extending from the outer contact surface 48 and comprising an elongated portion 53 and an elongated portion 54. The elongated portion 54 may be taller than the elongated portion 53 to provide the prosthetic device 30 with greater stability in the hard cortical bone of the outer wall of the vertebral body 14. In this embodiment, the raised keel portion 54 has a sharpened and undercut leading edge 56 to encourage aggressive cutting of a channel in the vertebral body 14 and endplate 18, which could help prevent the device 30 from skiving off the vertebral body 14. In this embodiment, the raised keel portion 54 is approximately one-third the length of the upper keel 52 and extends to the posterior edge of the upper joint component to provide additional stability. In alternative embodiments, the upper keel may be longer or shorter to achieve desired stability. If desired, the lower joint component 34 may include a lower keel 58 extending from the outer contact surface 50.

In various alternative embodiments, the width of the keel may vary. For example, the lower portion of the keel may be narrower than the taller portion of the keel. In other embodiments, the keel may taper or have an undulating wave form. In still another alternative, the keel may be perforated or porous to promote bone ingrowth.

The upper joint component 32 may further include a posterior tab 60 extending upward from the posterior edge of the outer contact surface 48. In this embodiment, the tab 60 may be generally perpendicular or slightly acutely angled relative to the contact surface 48. The tab 60 may be integrally formed with or otherwise abut the posterior end of the upper keel 52. As will be described in greater detail below, the posterior tab 60 may serve as a stop to prevent the device 30 from being inserted too far anteriorly into the intervertebral disc space. The position of the tab 60 may be monitored with fluoroscopy or other visualization methods during surgery to determine the progress of the implantation and to confirm when the device 30 has been completely implanted with the posterior tab 60 in contact with a posterior wall of the vertebral body 14. Because the position of the posterior tab 60 may be fixed relative to a center of rotation of the joint formed by articulation surfaces 36, 38, the location of the posterior tab 60 may serve as an indicator of the location of the center of rotation. After the surgeon has determined the desired location for the center of rotation, the upper joint component 32 may be selected so that as the posterior tab 60 is positioned against the posterior wall of the vertebral body 14, the center of rotation is moved into the desired predetermined location.

The prosthetic device 30 may further include a support or "bridge" component 62, which extends posteriorly from the lower joint component 34. As installed, the bridge component 62 will desirably further extend posteriorly from the intervertebral disc space between the vertebral bodies, with a lower surface that abuts and/or engages with at least a portion of the pedicle 25 to a distal end 64.

The distal end 64 of the bridge 62 may include a connection component 66, which in this embodiment is a passage for accepting a fastener 68. In this embodiment, the fastener 68 is a bone screw, however in alternative embodiments, fasteners such as nails, staples, or other mechanical or chemical fasteners may be suitable. The orientation of the connection component 66 desirably permits the fastener 68 to become inserted extrapedicularly, such that the screw travels a path obliquely angled or skewed away from a central axis defined through a pedicle. The fastener 68 may be threaded across a portion of the pedicle 25 and into the vertebral body 20. Extrapedicular fixation may be any fixation into the pedicle that does not follow a path down a central axis defined generally posterior-anterior through the pedicle. In this embodiment, the screw passes through a wall portion of the pedicle, whereby it may achieve strong cortical fixation. In all embodiments, the fasteners may be at least partially recessed so as not to interfere with articulations, soft tissues, and neural structures.

As installed, the bridge 62 and the fastener 68 may limit excessive movement of the device 30, particularly during flexion/extension motions. Additionally, the bridge 62 may distribute the loads on the lower vertebra V2, reducing any opportunity for subsidence of the lower joint component 34 into the vertebral body.

If desired, the connection component 66 may further include an optional locking clip 70, which in this embodiment is an elastically deformable C-shaped structure which holds the fastener 68 in place, resisting any backward disengagement of the fastener 68, particularly when the joint 12 is in motion. It is understood that in alternative embodiments, the locking clip may be a cap, a clamp, an adhesive, or other suitable mechanical or chemical systems for limiting movement of the fastener 68.

The size and shape of the joint components 32, 34 and the bridge component 62 may be limited by the constraints of a posterior surgical approach. For example, the anterior joint components 32, 34 may be configured to cover a maximum vertebral endplate area to dissipate loads and reduce subsidence while still fitting through the posterior surgical exposure, Kambin's triangle, and other neural elements. To achieve maximum surface coverage, the material of the anterior joint components 32, 34 may extend anteriorly from the articulation surfaces 36, 38, respectively. The width of the bridge component 62 may also be selected to desirably pass through Kambin's triangle and to co-exist with the neural elements, yet provide sufficient cross-sectional area to the pedicle structures for additional support.

In alternative embodiments, the upper and lower joint components may be provided in various heights. For example, the height of the upper component may be increased by manufacturing the component with a thickened contact surface. Likewise, material may be added to increase the overall height of the lower component. Providing the components in a variety of selectable heights may allow the surgeon to create the appropriate tension within the joint to both promote bone growth into the upper and lower components and to achieve a desired range of motion. In still other alternative embodiments, the heights of the upper and lower joint components may increase or decrease along the length of the component to create a desired lordosis or kyphosis. The ability to modify the resulting angle between the upper and lower vertebral contact surfaces may allow the surgeon to address variations among patient anatomies or between levels of the vertebral column, such as at the lumbosacral joint (L5-S1). Allowing the surgeon to vary the height, angulation, and performance of the prosthetic device based on the vertebral level or the patient's anatomy may ensure a better fit and a better prognosis for the patient.

For all of the embodiments described herein, the prosthetic device 30 may be formed of any suitable biocompatible material including metals such as cobalt-chromium alloys, titanium alloys, nickel titanium alloys, and/or stainless steel alloys. Ceramic materials such as aluminum oxide or alumina, zirconium oxide or zirconia, compact of particulate diamond, and/or pyrolytic carbon may also be suitable. Polymer materials may also be used, including any member of the polyaryletherketone (PAEK) family such as polyetheretherketone (PEEK), carbon-reinforced PEEK, or polyetherketoneketone (PEKK); polysulfone; polyetherimide; polyimide; ultra-high molecular weight polyethylene (UHMWPE); and/or cross-linked UHMWPE. The various components comprising the prosthetic device 30 may be formed of different materials thus permitting metal on metal, metal on ceramic, metal on polymer, ceramic on ceramic, ceramic on polymer, or polymer on polymer constructions.

In any one of the described embodiments, the bone contacting surfaces of the prosthetic device 30 including contact surfaces 48, 50; keels 52, 58; and bridge 62 may include features or coatings which enhance the fixation of the implanted prosthesis. For example, the surfaces may be roughened such as by chemical etching, bead-blasting, sanding, grinding, serrating, and/or diamond-cutting. All or a portion of the bone contacting surfaces of the prosthetic device 30 may also be coated with a biocompatible and osteoconductive material such as hydroxyapatite (HA), tricalcium phosphate (TCP), and/or calcium carbonate to promote bone in growth and fixation. Alternatively, osteoinductive coatings, such as proteins from transforming growth factor (TGF) beta superfamily, or bone-morphogenic proteins, such as BMP2 or BMP7, may be used. Other suitable features may include spikes, ridges, and/or other surface textures.

The prosthetic device 30 may be installed between the vertebrae V1, V2 as will be described below. The prosthetic device 30 may be implanted into a patient using a posterior transforaminal approach similar to the known TLIF (transforaminal lumbar interbody fusion) or PLIF (posterior lumbar interbody fusion) procedures. PLIF style approaches are generally more medial and rely on more retraction of the traversing root and dura to access the vertebral disc space. The space between these structures is known as Kambin's triangle. TLIF approaches are typically more oblique, requiring less retraction of the exiting root, and less epidural bleeding with less retraction of the traversing structures. It is also possible to access the intervertebral space using a far lateral approach, above the position of the exiting nerve root and outside of Kambin's triangle. In some instances, it may be possible to access the intervertebral space via the far lateral without resecting the facets. Furthermore, a direct lateral approach through the psoas is known. This approach avoids the posterior neural elements completely. Embodiments of the current disclosure may adopt any of these common approaches or combinations thereof.

In various embodiments, some or all of the affected disc D1 and surrounding tissue may be removed via the foramina. The superior endplate of the vertebra may be milled, rasped, or otherwise resected to match the profile of the outer contact surface 50 of the lower joint component 34 to normalize stress distributions on the endplate 24, and/or to provide initial fixation prior to bone ingrowth. The preparation of the endplate 24 of vertebra V2 may result in a flattened surface or in surface contours such as pockets, grooves, or other contours that may match corresponding features on the outer contact surface 50. The inferior endplate of the vertebra may be similarly prepared to receive the upper joint component 32 to the extent allowed by the exiting nerve root and the dorsal root ganglia. In various embodiments, the natural facet joint and the corresponding articular processes 16, 22 can be rasped and/or prepared to accommodate and/or support an outer surface of the bridge component 62.

Figure 10:
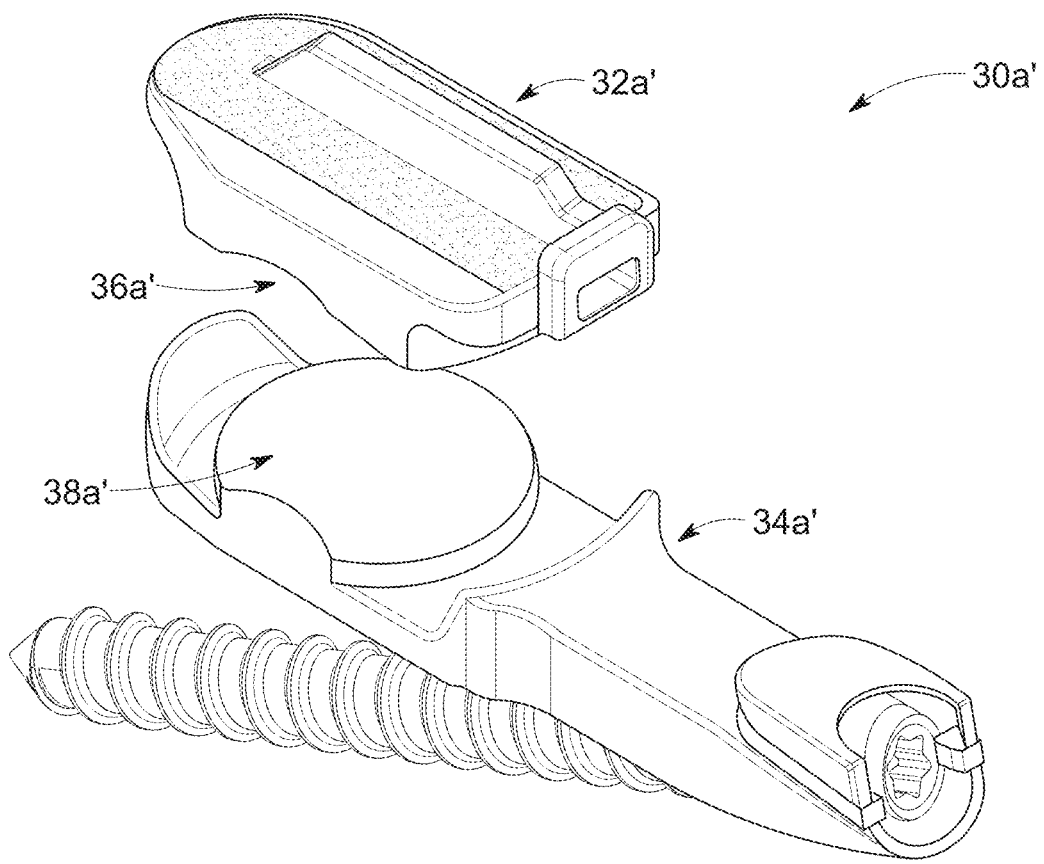
FIGS. 10 and 11 through 14 depict additional exemplary embodiments of prosthetic devices which allow for significant resection of a vertebral body and/or pedicle and associated spinal structures.
Figure 11:
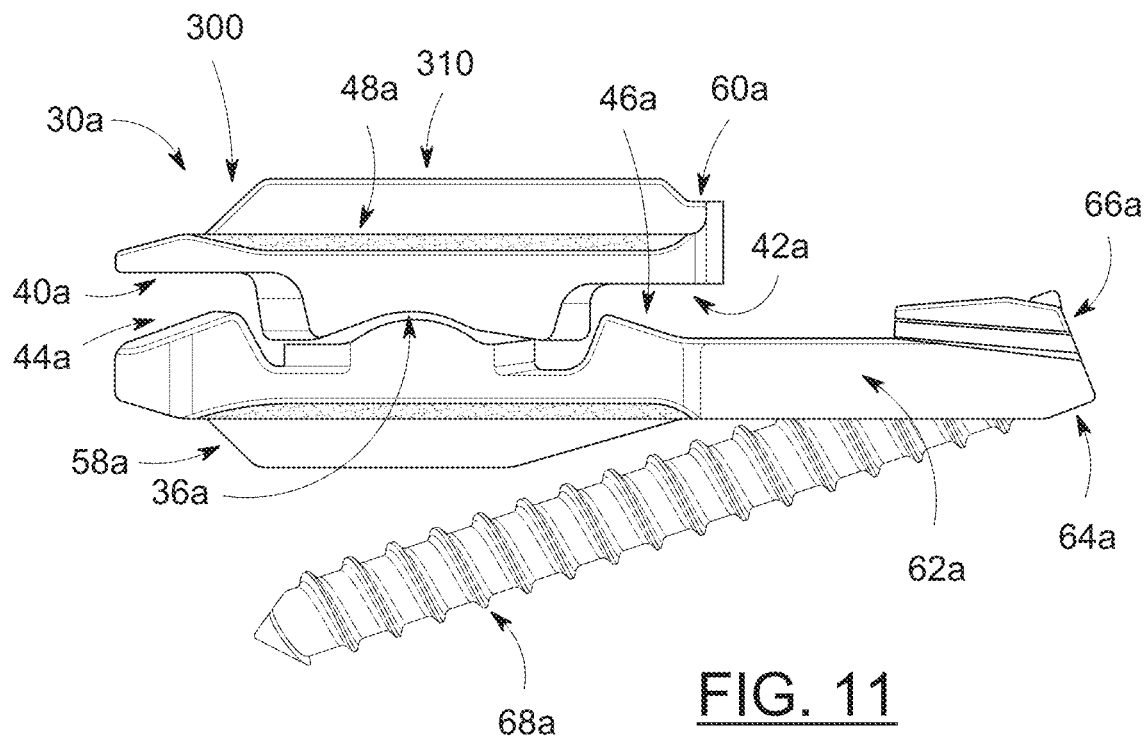
Figure 12:
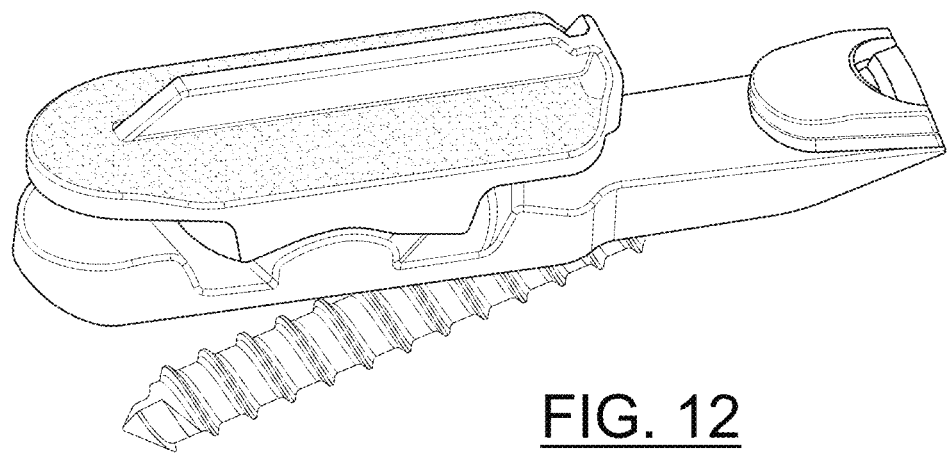
Figure 13:
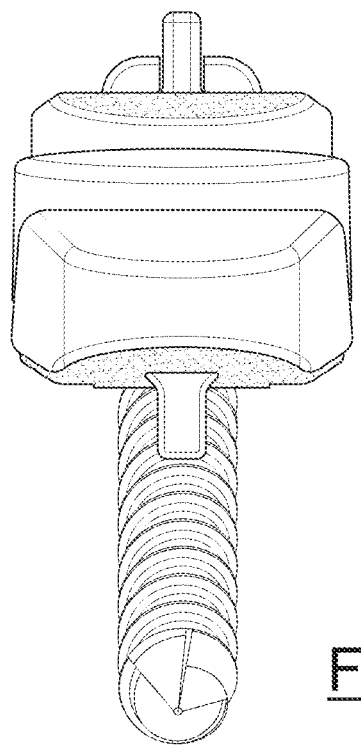
Figure 14:
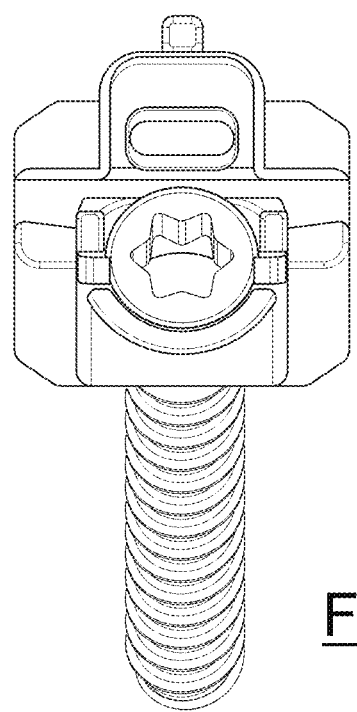
Figure 15A:
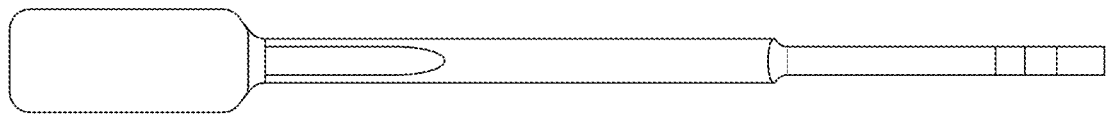
FIGS. 15A through 16C depict exemplary surgical rasps for preparing vertebral anatomy.
Figure 15B:
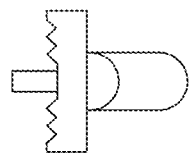
Figure 16A:
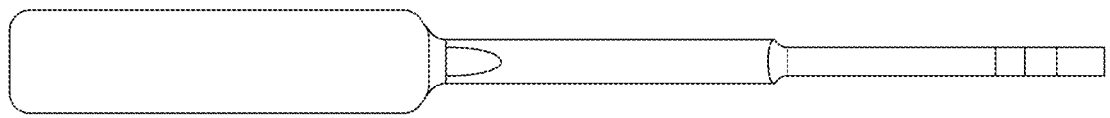
Figure 16B:
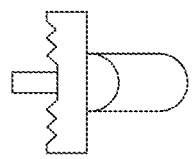
Figure 16C:
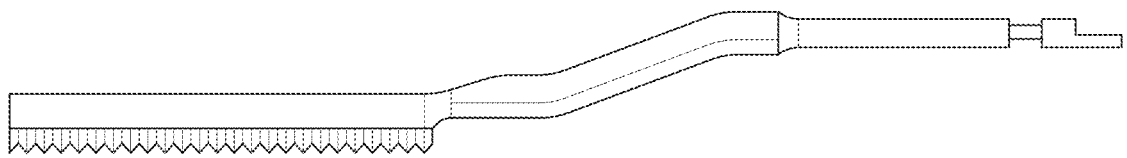
Figure 17A:
FIGS. 17A through 17E depict cross-sectional views of exemplary rasps and alignment tools for use in preparing spinal anatomy.
Figure 17B:
Figure 17C:
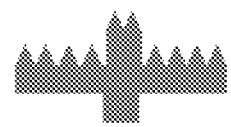
Figure 17D:
Figure 17E:

FIGS. 10 and 11 through 14 depict views of additional alternative embodiments of prosthetic devices constructed in accordance with various teaching of the present invention. In the embodiment of FIG. 10, the prosthetic device 30a' can include an upper joint component 32a' and a lower joint component 34a', with the upper joint component 32a' including an articulation surface 36a', and the lower joint component 34a' including an articulation surface 38a'. When assembled, the articulation surface 36a' may engage the articulation surface 38a' to produce a ball-and-socket style anterior joint. It should be understood that the various features described in connection with FIGS. 11 through 14 can be incorporated with similar utility to the embodiment of FIG. 10.

In the embodiment of FIGS. 11 through 14, the prosthetic device 30a can include an upper joint component 32a and a lower joint component 34a, with the upper joint component 32a including an articulation surface 36a, and the lower joint component 34a including an articulation surface 38a. When assembled, the articulation surface 36a may engage the articulation surface 38a to produce a ball-and-socket style anterior joint. The upper joint component 32a can further include bumpers or motion limiters 40a and 42a, which in this embodiment are depicted as recessed shoulders. The lower joint component 34a can also include bumpers or motion limiters 44a and 46a, which in this embodiment are upwardly protruding extensions, spaced apart from the articulation surface 38a. In a manner similar to the previously described embodiments, the pair of motion limiters 40a and 44a and the pair of motion limiters 42a and 46a may serve to constrain flexion/extension motion to a desirable range, preventing or limiting the dislocation of the joint formed by the articulation surfaces 36a and 38a. The motion limiters may be shaped to provide a greater or lesser range of flexion/extension motion. For example, a surface on the motion limiter 44a angled away from the articulation surface 38a may permit greater flexion motion than would a motion limiter surface parallel to an axis of the spine.

The upper joint component 32a may further include an outer contact surface 48a for interfacing with a lower surface of the upper vertebral endplate, and the lower joint component 34a may include an outer contact surface 50a for interfacing with a upper surface of the lower vertebral endplate, the lower vertebral pedicle and/or other surfaces of the lower vertebral body.

The upper joint component 32a may further include an upper keel 300 extending from the outer contact surface 48a and comprising an elongated portion 310. The elongated portion 310 will desirably extend upward from the outer contact surface 48a, to provide the prosthetic device 30a with greater stability in the upper vertebral body. In this embodiment, the upper keel portion 300 may have a sharpened and/or undercut leading edge, if desired. In alternative embodiments, the upper keel may be longer or shorter to achieve desired stability. If desired, the lower joint component 34a may include a lower keel 58a extending from the outer contact surface 50a.

In various alternative embodiments, the width of the keel may vary. For example, the lower portion of the keel may be narrower than the taller portion of the keel. In other embodiments, the keel may taper or have an undulating wave form. In still another alternative, the keel may be perforated or porous to promote bone ingrowth.

In various embodiments, the upper joint component 32a may further include a posterior tab 60a extending upward from the posterior edge of the outer contact surface 48a. In this embodiment, the tab 60a may be generally perpendicular or slightly acutely angled relative to the contact surface 48a. The tab 60a may be integrally formed with or otherwise abut the posterior end of the upper keel 300. In a manner similar to previously described embodiments, the posterior tab 60a may serve as a stop to prevent the device 30a from being inserted too far anteriorly into the intervertebral disc space. The position of the tab 60a may be monitored with fluoroscopy or other visualization methods during surgery to determine the progress of the implantation and to confirm when the device 30a has been completely implanted with the posterior tab 60a in contact with a posterior wall of the vertebral body. Because the position of the posterior tab 60a may be fixed relative to a center of rotation of the joint formed by articulation surfaces 36a and 38a, the location of the posterior tab 60a may serve as an indicator of the location of the center of rotation. After the surgeon has determined the desired location for the center of rotation, the upper joint component 32a may be selected so that as the posterior tab 60a is positioned against the posterior wall of the vertebral body, the center of rotation is moved into the desired predetermined location.

The prosthetic device 30a will desirably further include a support or "bridge" component 62a, which extends posteriorly from the lower joint component 34a. As installed, the bridge component 62a will desirably further extend posteriorly from the intervertebral disc space between the vertebral bodies, with a lower surface that abuts and/or engages with at least a portion of a pedicle (and/or other vertebral structures) to a distal end 64a.

The distal end 64a of the bridge 62a may include a connection component 66a, which in this embodiment is a passage for accepting a fastener 68a. In this embodiment, the fastener 68a is a bone screw, however in alternative embodiments, fasteners such as nails, staples, or other mechanical or chemical fasteners may be suitable. The orientation of the connection component 66a desirably permits the fastener 68a to become inserted extrapedicularly, such that the screw travels a path obliquely angled or skewed away from a central axis defined through a pedicle. The fastener 68a may be threaded across a portion of the pedicle and into the vertebral body. Extrapedicular fixation may be any fixation into the pedicle that does not follow a path down a central axis defined generally posterior-anterior through the pedicle. In this embodiment, the screw may pass through a wall portion of the pedicle and/or vertebral body, whereby it may achieve strong cortical fixation. In all embodiments, the fasteners may be at least partially recessed so as not to interfere with articulations, soft tissues, and neural structures.

As previously noted, alternative embodiments of the upper and lower joint components may be provided in various heights. For example, the height of the upper component may be increased by manufacturing the component with a thickened contact surface. Likewise, material may be added to increase the overall height of the lower component. Providing the components in a variety of selectable heights may allow the surgeon to create the appropriate tension within the joint to both promote bone growth into the upper and lower components and to achieve a desired range of motion and/or spinal alignment. In still other alternative embodiments, the heights of the upper and lower joint components may increase or decrease along the length of the component to create a desired lordosis or kyphosis and/or accommodate a desired surgical resection and/or correction. The ability to modify the resulting angle between the upper and lower vertebral contact surfaces may allow the surgeon to address variations among patient anatomies or between levels of the vertebral column, such as at the lumbosacral joint (L5-S1). Allowing the surgeon to vary the height, angulation, and performance of the prosthetic device based on the vertebral level or the patient's anatomy may ensure a better fit and a better prognosis for the patient.

Exemplary Surgical Procedure

According to at least one embodiment, a first surgical incision for providing access via a bilateral approach is made in the patient's back, and a decompression of the posterior vertebral elements on a first posterior side of the spinal motion unit (i.e., removal of portions of the upper and/or lower facets on the medial side, for example) or other standard bilateral decompression can be accomplished to provide access to the intervertebral disc space. A discectomy can then be accomplished through the access, and a distractor/trial can be placed between the vertebral bodies, with the overlying skin and tissues allowed to relax. A second surgical incision is made to provide access to the opposing (i.e., lateral) side of the spinal motion unit, and then a similar decompression and discectomy can be accomplished through the lateral access.

The surgeon can then rasp, resect and/or otherwise remove portions of the vertebral body, the pedicle and/or other posterior structures of the vertebral body, including portions of the upper endplate of the lower vertebral body, in accordance with the preoperative surgical plan. In various embodiments, a long flat rasp 300 (see FIG. 18) can be utilized to remove and prepare the upper surface of the lower vertebral body and pedicle, and a short rasp 305 can be similarly used on the lower endplate of the upper vertebral body, such as to flatten or otherwise prepare the top of the disc space. Once the upper surface of the lower vertebral body has been prepared using the flat rasp, a long keel rasp 310 can be utilized to prepare a keel slot or similar feature in the vertebral body and/or pedicle. A short rasp with a non-cutting index 315 can then be utilized to mark the top keel and align it with the cut along the pedicle, and then the top keel groove can be formed in the upper vertebral body using the short keeled rasp 305.

Once one side of the vertebral body and disc space have been prepared in this fashion, a spacer or trial may be placed into the disc space to ensure the vertebral bodies have been properly prepared, that a desired angular correction has been established, and/or that a desired tension of the lateral annulus will be achieved once the final implant has been emplaced. If the trial/spacer appears to properly fit, then the trial/spacer can be removed and replaced with the assembled implant. Once the assembled implant is in a desired position, an anchoring screw or other anchoring device can be inserted through the connection component and secured to the lower vertebral body.

In various embodiments, the long flat rasp or other surgical tool(s) could be attached to a surgical guidance system, allowing a surgeon to view the predicted and/or actual path of the rasp/tool on the targeted anatomy. Various additional steps of the procedure as outlined could be accomplished using a surgical guidance system, with at least one benefit of surgical guidance potentially reducing radiation exposure to the patient and/or operative room personnel while enhancing the accuracy and/or fidelity of the anatomical preparation by matching the preoperative plan with the intraoperative execution in three dimensions.

In other alternative embodiments, the various steps described herein could be accomplished with the aid of a surgical robot, with or without surgical navigation. In one embodiment, the surgical robot could provide haptic feedback to the surgeon, which might desirably notify the surgeon of approaching soft tissues and/or other surgical boundaries. In another embodiment, the robot could provide rigid limits for surgeon activity (i.e., to prevent cutting into delicate tissues, for example). In a third embodiment, the surgical robot could complete surgical steps autonomously (i.e., with or without surgeon intervention). The employment of surgical robots as outlined could potentially reduce radiation exposure to the patient and/or operative room personnel while enhancing the accuracy and/or fidelity of the anatomical preparation by matching the preoperative plan with the intraoperative execution in three dimensions.

Once one side of the vertebral body has been treated in the previous manner, the same approach can be repeated on the other side of the vertebral body, including trialing and placement of the final implant. One particularly advantageous feature of the present invention is that the disclosed technique allows a surgeon to trial and "balance" the medial and lateral annulus for proper tension/laxity, in a manner similar to balancing of a knee implant. Such balancing, which is not currently possible using existing devices and surgical techniques, can significantly improve the stability and performance of the spinal implant, and can also contribute greatly to device function and durability, as well as significantly reduced patient pain and/or recovery time, leading to increased patient satisfaction with this procedure.

Figure 19:
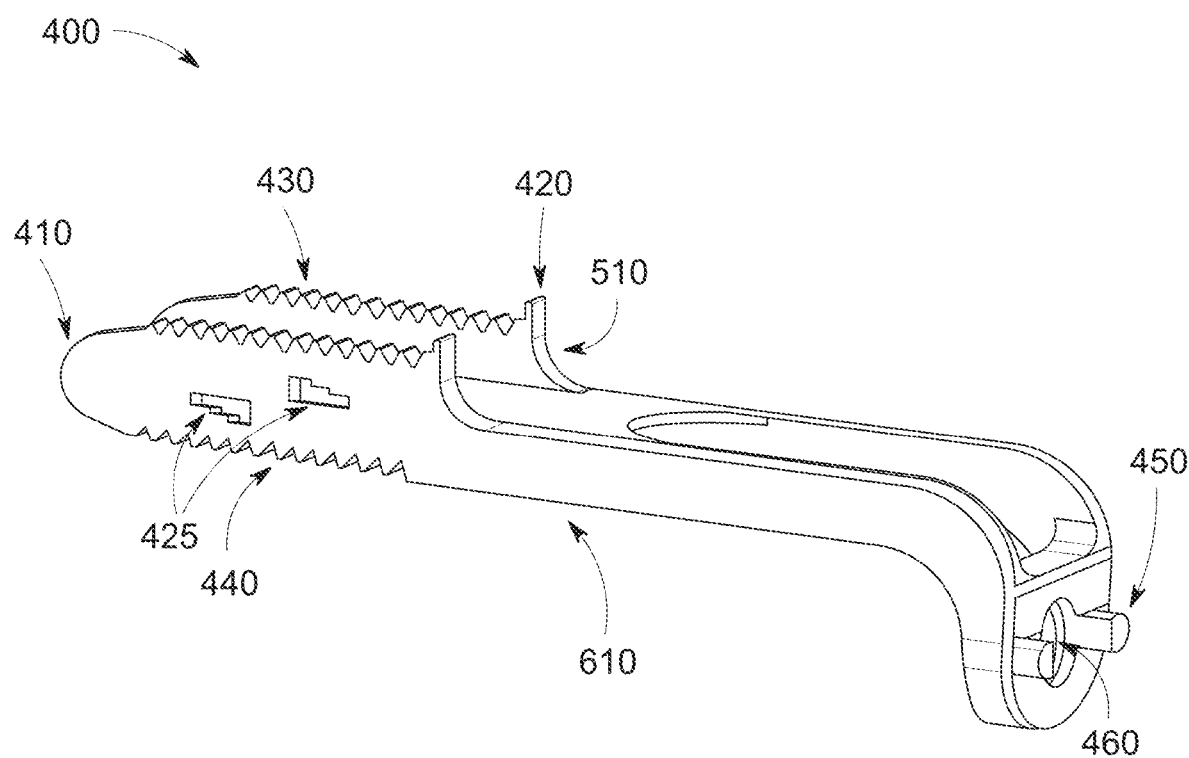
FIG. 19 depicts a perspective view of one exemplary embodiment of a trial and rasp guide.

FIG. 19 depicts one exemplary embodiment of a trial and rasp guide 400, which could be used with various embodiments of the present invention. The guide 400 can be provided in kit of guides of differing heights, including kits having one or more guides with heights of 8 mm, 9 mm, 10 mm, 11 mm, 12 mm, 13 mm, 14 mm and/or the like. In this embodiment, the guide 400 can include a bullet nose 410 which gradually increases to the full height of the guide (allowing for insertion of the guide into spaces that are somewhat more narrow than the full guide height), a depth stop 420, one or more depth indicator windows 425, an upper textured surface 430 (which could be a toothed pattern or other pattern), a lower texture surface 440, an insertion instrument attachment point 450 and an anchor receiver 460. Desirably, the anchor receiver 460 will be sized and configured to accept a pedicle screw or other anchoring device therein.

Figure 20A:
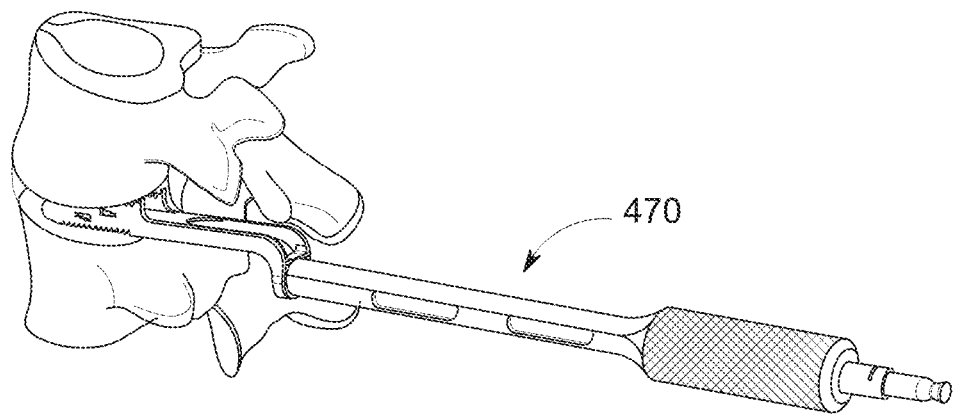
FIGS. 20A through 20F and 21A through 21C depict exemplary steps for using the guide of FIG. 19 in preparing a functional spinal unit for an implant.
Figure 20B:
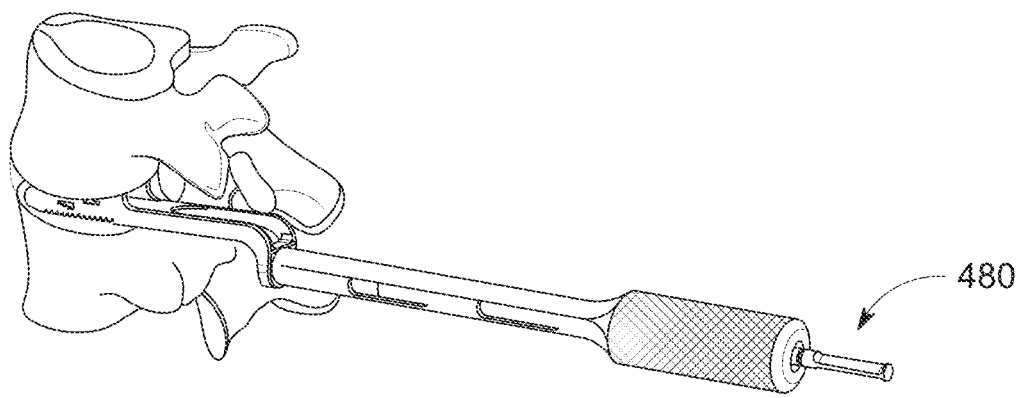
Figure 20C:
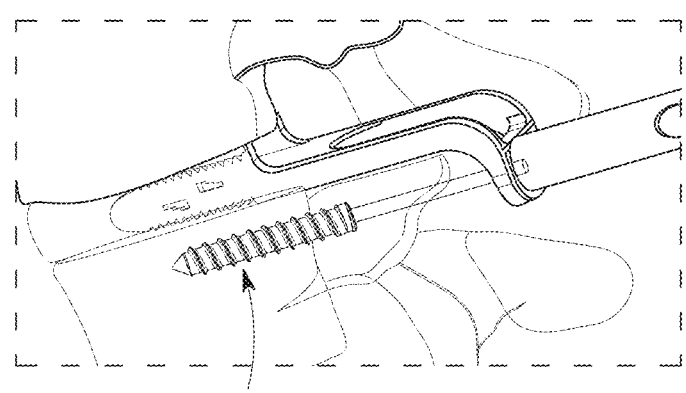
Figure 20D:
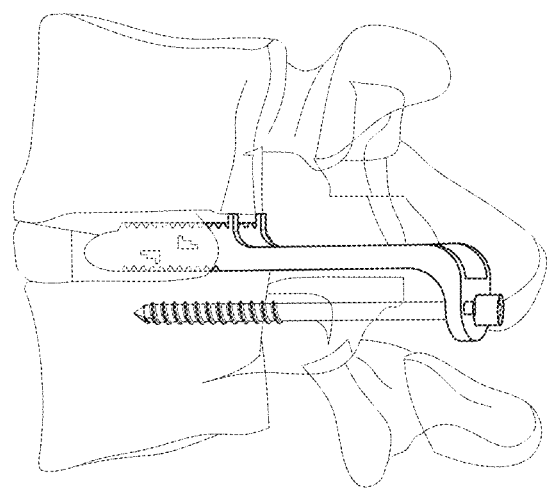
Figure 20E:
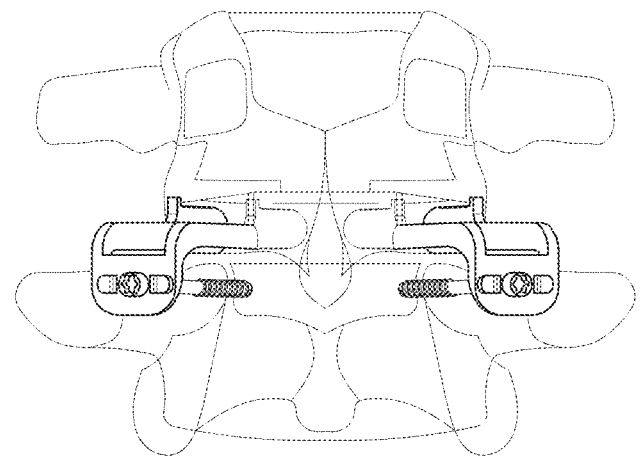
Figure 20F:
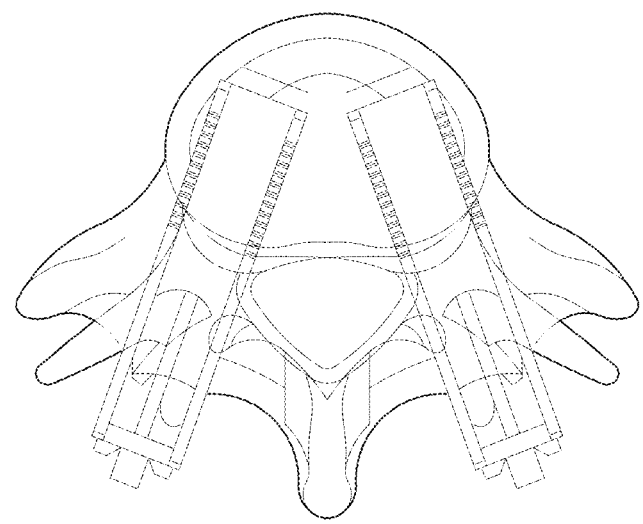

In use, the guide 400 can be attached to a placement tool 470 (see FIG. 20A) and inserted into one side of a functional spinal unit after the posterior elements have been removed, and the disc space initially prepared. The positioning and/or placement of the guide 400 will desirably be monitored and/or controlled using fluoroscopic or other guidance, and then a threaded inner rod 480 (see FIG. 20B) of the placement tool 470 can be removed and a pilot anchor hole (not shown) can be drilled into the vertebral body. A pedicle pin 490 or other anchoring device (see FIG. 20C) can then be placed into the vertebral body through the placement tool and the tool 470 can be removed. A second guide 405 can then be placed into the other side of the functional spinal unit, and the guide placement and orientation can be verified using fluoroscopy or other imaging techniques, as well as via direct visualization (See FIGS. 20D through 20F).

Figure 21A:
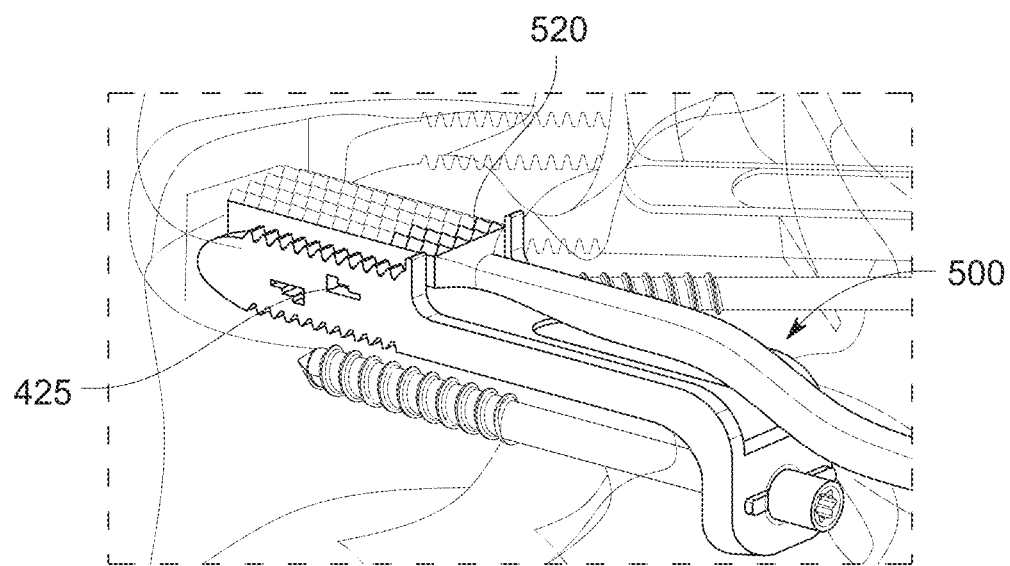
Figure 21B:
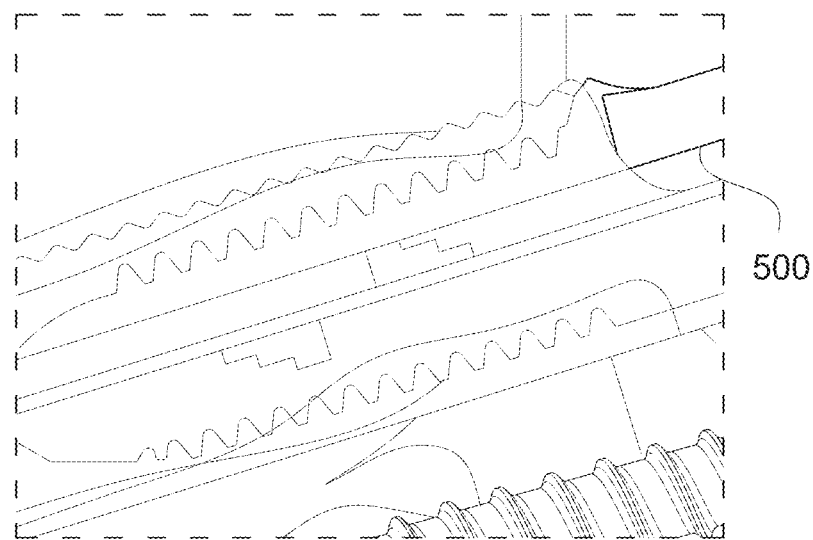

A rasp 500 can then be inserted into an upper channel 510 of the guide 400 (see FIG. 21A) to begin superior endplate bone preparation, and the rasp anterior depth can be monitored and/or limited by aligning a proximal end 520 of the rasp with the posterior vertebral wall of the upper vertebral body. The depth of rasping into the upper endplate can be monitored and/or controlled using the depth indicator windows 425, which can be monitored fluoroscopically. In the exemplary embodiment, each step of a cutout in the depth indicator windows 425 can represent 0.5 mm increments, although other depth increments may be preferred. The depth of the rasp is desirably indicated by the smooth (i.e., non-cutting) side of the rasp which aligns with steps in the depth indicator window 425 (see FIG. 21B). When a desired shape and extent of upper endplate preparation is achieved, the rasp 500 can then be removed.

Figure 21C:
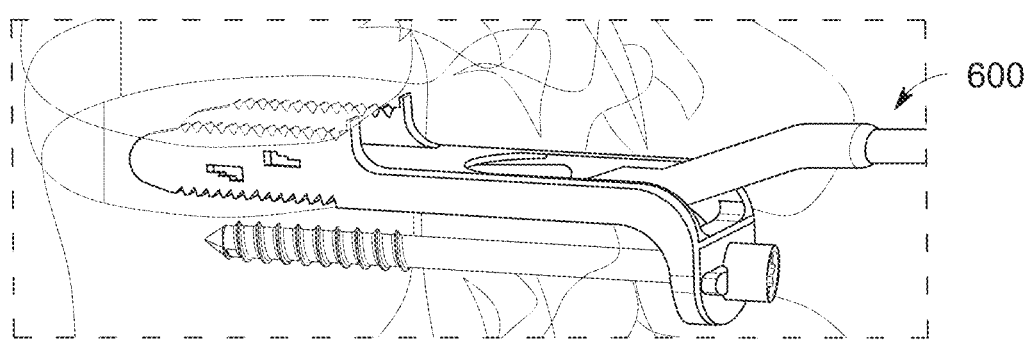

A long rasp 600 can then be inserted into a lower channel 610 of the guide 400, with the rasp used to cut and prepare the lower vertebral endplate, pedicle and/or other vertebral structures (see FIG. 21C) in a manner similar to the upper endplate, including the use of the depth stop to monitor rasping depth. Once the lower endplate preparation is complete, similar steps can be taken to prepare the vertebral bodies on the contralateral side of the spinal motion unit, and then placement of the spinal prostheses could be effectuated.

Spinal Fusion Implants

Figure 22:
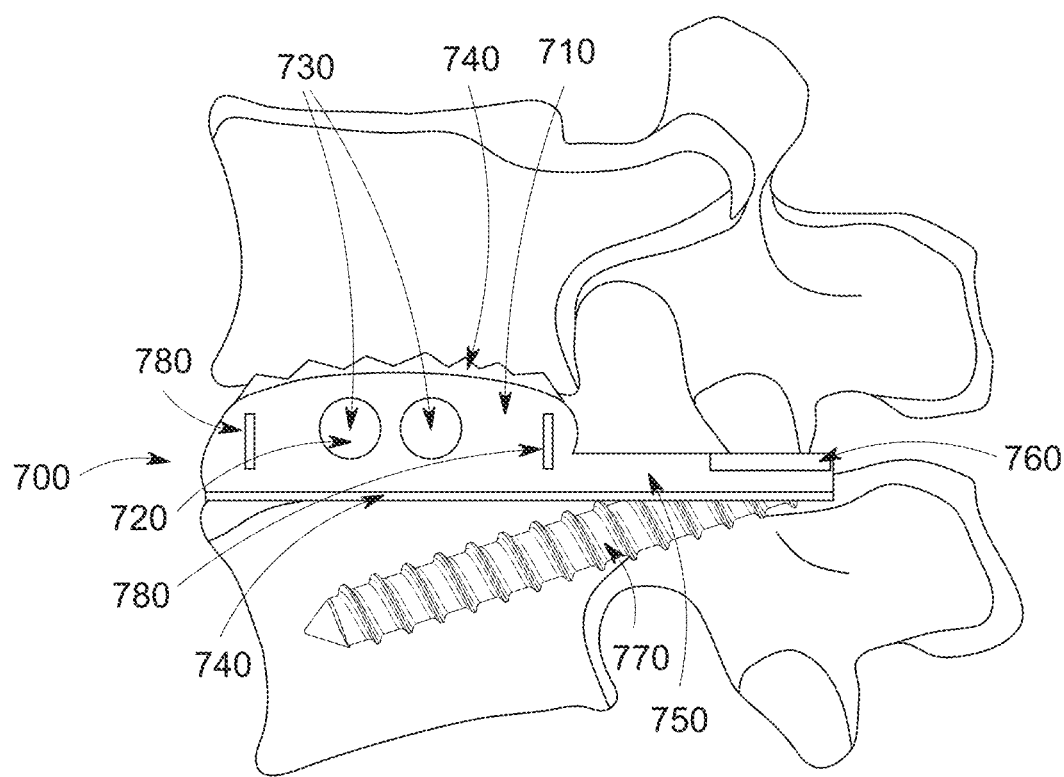
FIG. 22 depicts a side view of one embodiment of a fusion implant for use with various teachings of the present invention.

In various embodiments, a spinal fusion device may be implanted into a functional spinal unit for a variety of reasons, including to restore stability to a significantly degraded and/or unstable spinal level. FIG. 22 depicts one exemplary embodiment of a fusion implant 700 that could be implanted bilaterally in a manner similar to the embodiments previously described. In this embodiment, the fusion implant 700 includes a central body 710 having an open graft window 720 with side ports 730 for graft cell placement, ingrowth or on-growth surfaces 740 for bony integration with the adjacent vertebral surfaces, a bridge or tail 750 for integrating with the prepared pedicle surfaces (i.e., to prevent subsidence and/or to cross the foramen) and a screw or anchor retention feature 760 for accommodating an anchoring screw 770. In addition, the implant 700 could desirably include radiopaque markers 780 or other features to allow the position and/or orientation of the implant 700 to be monitored in a non-invasive manner after surgery.

Figure 23:
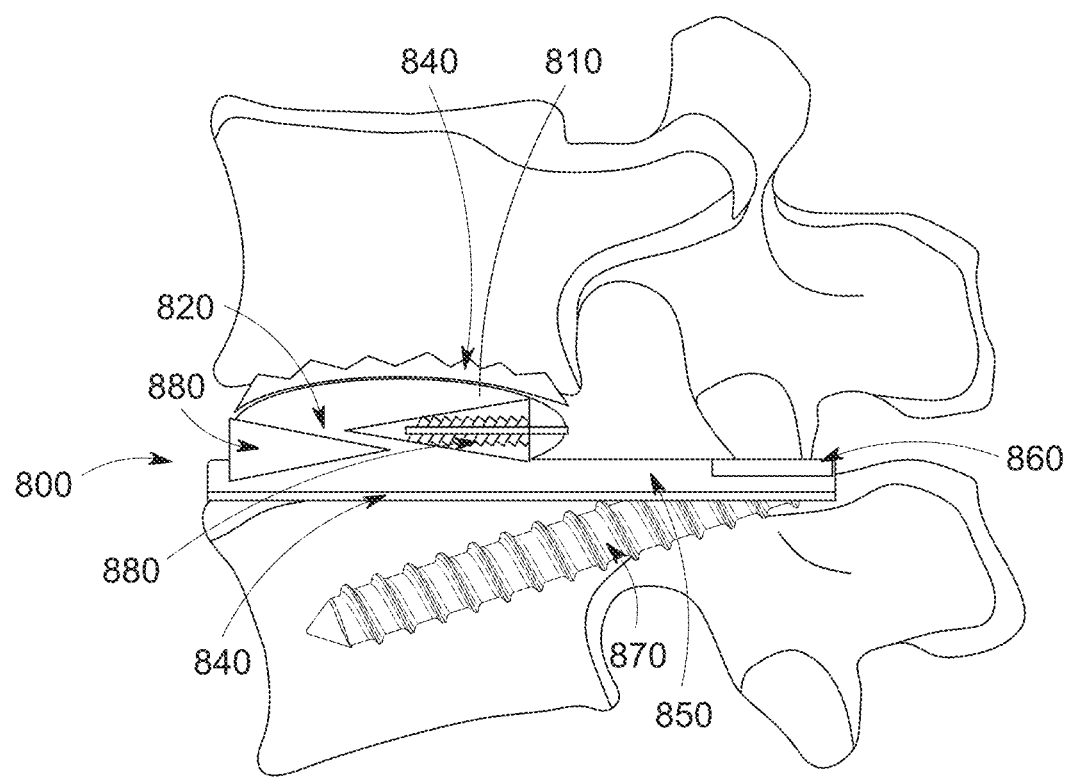
FIG. 23 depicts a side view of one embodiment of an expandable fusion implant for use with various teachings of the present invention.

FIG. 23 depicts another alternative embodiment of a fusion implant 800, which desirably allows for expansion and/or modification of the implant height during surgery. In this embodiment, the implant 800 includes a central body 810 having an optional open graft window 820 with side ports (not shown) for graft cell placement, ingrowth or on-growth surfaces 840 for bony integration with the adjacent vertebral surfaces (which could include milled and/or freehand techniques—i.e., anatomical fit), a bridge or tail 850 for integrating with the prepared pedicle surfaces (i.e., to prevent subsidence and/or to cross the foramen) and a screw or anchor retention feature 860 for accommodating an anchoring screw 870. In addition, the implant 800 desirably includes wedges of other expansion features 880, which could include vertical-only expansion, sagittal expansion and/or some combination of vertical/sagittal expansion.

INCORPORATION BY REFERENCE

The entire disclosure of each of the publications, patent documents, and other references referred to herein is incorporated herein by reference in its entirety for all purposes to the same extent as if each individual source were individually denoted as being incorporated by reference.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus intended to include all changes that come within the meaning and range of equivalency of the descriptions provided herein.

Many of the aspects and advantages of the present invention may be more clearly understood and appreciated by reference to the accompanying drawings. The accompanying drawings are incorporated herein and form a part of the specification, illustrating embodiments of the present invention and together with the description, disclose the principles of the invention.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the disclosure herein. What have been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. A spinal prosthetic implant system for implantation between an upper and lower vertebra, comprising:
   a first spinal prosthetic implant, the first spinal prosthetic implant comprising a first upper joint component and a first lower joint component, the first upper joint component comprising an upwardly facing bone engagement surface and a cortical wall engaging portion, a concave shaped first upper articulation surface and a first upper bumper, the first upper, the first lower joint component comprising a convex shaped first lower articulation surface and a first lower bumper, the first upper and lower bumpers positioned between the first upper and lower joint components, the first lower bumper spaced apart from the first lower articulation surface, the first upper articulation surface of the first upper joint component engaging with the first lower articulation surface of the first lower joint component to create a first ball-and-socket joint that permits the first upper joint component to articulate relative to the first lower joint component; and a second spinal prosthetic implant, the second spinal prosthetic implant comprising a second upper joint component and a second lower joint component, the second upper joint component comprising a second upper articulation surface, the second upper articulation surface includes a concave shape, the second lower joint component comprising a second lower articulation surface, the second lower articulation surface includes a convex shape, the second upper articulation surface of the second upper joint component engages with the second lower articulation surface of the second lower joint component to create a second ball-and-socket joint that permits the second upper joint component to rotate and articulate relative to the second lower joint component;

the first spinal implant adapted for placement in a first orientation between the upper and lower vertebra and the second spinal implant adapted for placement in a second orientation between the upper and lower vertebra.

2. The spinal prosthetic implant system of claim 1, wherein the first upper joint component follows a first motion path relative to the first lower joint component and the second upper joint component follows a second motion path relative to the second lower joint component, and the first motion path comprises the same motion as the second motion path.

3. The spinal prosthetic implant system of claim 2, wherein the same motion comprises flexion, extension, lateral bending, and rotational motion.

4. The spinal prosthetic implant system of claim 1, wherein the first orientation of the first spinal prosthetic implant is the same orientation as the second orientation of the second prosthetic implant.

5. The spinal prosthetic implant system of claim 1, wherein the first orientation and the second orientation comprise an angled orientation.

6. The spinal prosthetic implant system of claim 1, wherein the first orientation and the second orientation are symmetrical.

7. The spinal prosthetic implant system of claim 1, wherein the first lower joint component of the first spinal prosthetic implant further comprises a first lower bridge that extends posteriorly from a posterior end of the first lower joint component, and the second lower joint component of the second spinal prosthetic implant further comprises a second lower bridge that extends posteriorly from a posterior end of the second lower joint component.

8. The spinal implant system of claim 7, wherein the first lower bridge comprises a first connection component, the first connection component comprising a first passageway, the first passageway sized and configured to receive a first fastener, and the second lower bridge comprises a second connection component, the second connection component comprising a second passageway, the second passageway sized and configured to receive a second fastener.

9. The spinal implant system of claim 8, wherein the first passageway of the first connection component comprises a first axis, the first axis is positioned obliquely, and the second passageway of the second connection component comprises a second axis, the second axis is positioned obliquely.

10. The spinal implant system of claim 8, wherein the first connection component of the first lower bridge comprises a first locking clip, the first locking clip comprises a first disengagement portion contacting a first top surface of the first fastener to resist backward disengagement, and the second connection component of the second lower bridge comprises a second locking clip, the second locking clip comprises a second disengagement portion contacting a second top surface of the second fastener to resist backward disengagement.

11. The spinal implant system of claim 1, wherein the cortical wall engaging portion comprises a generally perpendicular tab extending upwardly from the bone engagement surface.

12. The spinal implant system of claim 1, wherein the cortical wall engaging portion is adjacent to the upwardly facing bone engagement surface.

13. The spinal implant system of claim 1, wherein the cortical wall engaging portion is angled relative to the upwardly facing bone engagement surface.

14. The spinal implant system of claim 1, wherein the cortical wall engaging portion is positioned at a first end of the first upper joint component.

15. The spinal implant system of claim 1, wherein the cortical wall engaging portion is radiopaque.

16. The spinal implant system of claim 1, wherein the cortical wall engaging portion comprises a posterior tab having a surface adapted to engage a posterior wall of the upper vertebrae.

17. The spinal implant system of claim 1, wherein the first upper joint component and first lower joint component are not fastened together.

* * * * *